US009132148B2

(12) United States Patent
Unger

(10) Patent No.: US 9,132,148 B2
(45) Date of Patent: Sep. 15, 2015

(54) GENE SILENCING BY SINGLE-STRANDED POLYNUCLEOTIDES

(71) Applicant: GeneSegues, Inc., Chaska, MN (US)

(72) Inventor: Gretchen M. Unger, Chaska, MN (US)

(73) Assignee: GeneSegues, Inc., Chaska, MN (US)

( * ) Notice: Subject to any disclaimer, the term of this patent is extended or adjusted under 35 U.S.C. 154(b) by 0 days.

(21) Appl. No.: 13/848,249

(22) Filed: Mar. 21, 2013

(65) Prior Publication Data

US 2013/0267577 A1 Oct. 10, 2013

Related U.S. Application Data

(63) Continuation of application No. 12/525,652, filed as application No. PCT/US2008/052863 on Feb. 1, 2008, now abandoned.

(60) Provisional application No. 60/898,674, filed on Feb. 1, 2007.

(51) Int. Cl.

*A61K 31/7125* (2006.01)
*C12N 15/11* (2006.01)
*C12N 15/113* (2010.01)

(52) U.S. Cl.

CPC .......... *A61K 31/7125* (2013.01); *C12N 15/111* (2013.01); *C12N 15/113* (2013.01); *C12N 2310/11* (2013.01); *C12N 2310/14* (2013.01); *C12N 2310/315* (2013.01); *C12N 2310/321* (2013.01); *C12N 2310/51* (2013.01)

(58) Field of Classification Search

USPC ......... 435/6.1, 91.1, 455, 375, 91.31; 514/44; 536/23.1, 24.5

See application file for complete search history.

(56) References Cited

U.S. PATENT DOCUMENTS

2008/0119530 A1 5/2008 Hansen
2010/0041047 A1 2/2010 Vickers
2010/0143500 A1 6/2010 Lawler

OTHER PUBLICATIONS

Agrawal et al., Molecular Med. Today, vol. 6, pp. 72-81 (2000).*
Peracchi et al, Rev. Med. Virol., vol. 14, pp. 47-64 (2004).*
Jang et al., Expert Rev. Medical Devices, vol. 1, No. 1, pp. 127-138 (2004).*
Opalinska et al, Nature Rev., vol. 1, pp. 503-514 (2002).*
Chirila et al., Biomaterials, vol. 23, pp. 321-342 (2002).*
Crooke, S., Progress in Antisense Technology, Ann. Rev. Medicine, vol. 55, pp. 61-95 (2004).*
Lima and Crooke (1997) Journal of Biological Chemistry 272(44):27513-27516, "Cleavage of Single Strand RNA Adjacent to RNA-DNA Duplex Regions by *Escherichia coli* RNase H1".
Monia, et al. (1993) Journal of Biological Chemistry 268(19):14514-14522, "Evaluation of 2'-Modified Oligonucleotides Containing 2'-Deoxy Gaps as Antisense Inhibitors of Gene Expression".
Reynolds, et al. (2004) Nature Biotechnology 22(3):326-330, "Rational siRNA Design for RNA Interference".
Schwartz, et al. (2002) Molecular Cell 10:537-548, "Evidence that siRNAs Function as Guides, Not Primers, in the *Drosophila* and Human RNAi Pathways".
Vickers, et al. (2003) Journal of Biological Chemistry 278(9):7108-7118, "Efficient Reduction of Target RNAs by Small Interfering RNA and RNase H-dependent Antisense Agents".

* cited by examiner

*Primary Examiner* — Jane Zara
(74) *Attorney, Agent, or Firm* — Swanson & Bratschun, L.L.C.

(57) ABSTRACT

The present invention relates to compositions and methods for concurrently activating antisense and double-stranded RNase (dsRNase) mechanisms for inhibiting expression of a targeted gene, by delivering a single stranded bifunctional chimeric DNA/RNA oligonucleotide optimized for siRNA activity as well as antisense activity, into the nucleus of a target cell.

2 Claims, 2 Drawing Sheets

Figure 1 Single-stranded chimeric polynucleotides bind nuclear Argo2 in cells plated on relevant protein matrices.
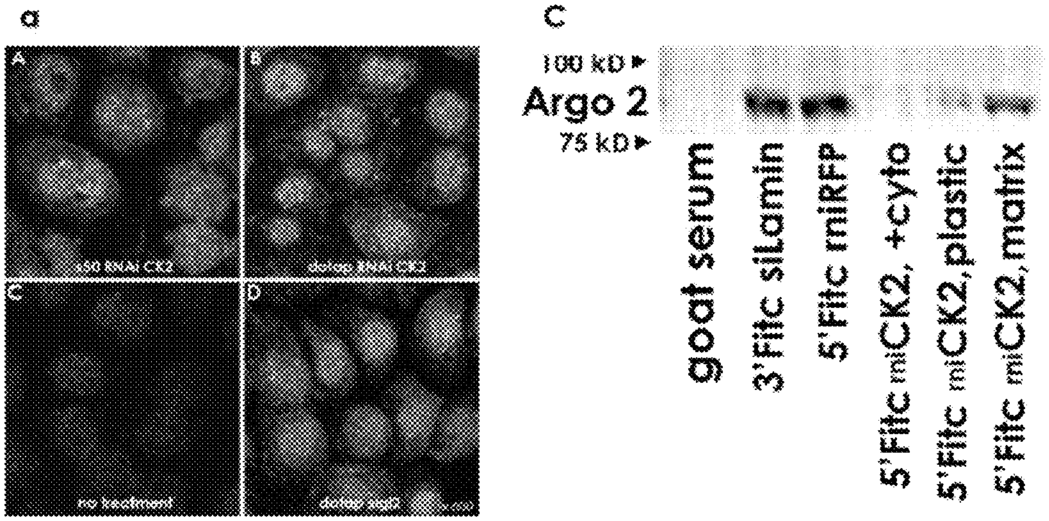
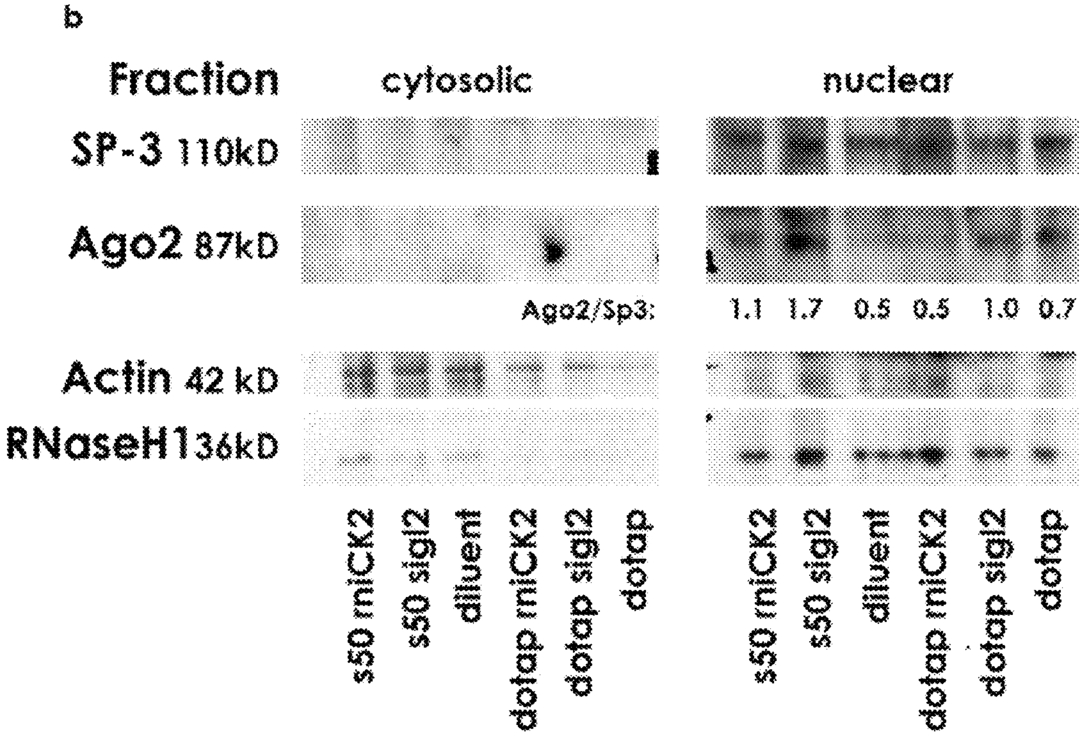

```
                         SEQUENCE LISTING


<160> NUMBER OF SEQ ID NOS: 12

<210> SEQ ID NO 1
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1

cuacacaaau cagcgauuuu u                                              21


<210> SEQ ID NO 2
<211> LENGTH: 22
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 2

aagccaauau ugaaacccac gg                                             22


<210> SEQ ID NO 3
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: misc_feature
<223> OTHER INFORMATION: Description of Combined DNA/RNA Molecule:
      Synthetic oligonucleotide

<400> SEQUENCE: 3

aacaggtatt cgctggucac                                                20


<210> SEQ ID NO 4
<211> LENGTH: 29
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 4

uguucuucug gaaguccagu uccuccuuc                                      29
```

-continued

```
<210> SEQ ID NO 5
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 5

ccaagaagcc cgugcagcu                                                19


<210> SEQ ID NO 6
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: misc_feature
<223> OTHER INFORMATION: Description of Combined DNA/RNA Molecule:
      Synthetic oligonucleotide

<400> SEQUENCE: 6

atacaaccca aactccacat                                               20


<210> SEQ ID NO 7
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: misc_feature
<223> OTHER INFORMATION: Description of Combined DNA/RNA Molecule:
      Synthetic oligonucleotide

<400> SEQUENCE: 7

gtcccgacat gtcagacagg                                               20


<210> SEQ ID NO 8
<211> LENGTH: 18
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 8

cguacgcgga aucuucga                                                 18


<210> SEQ ID NO 9
<211> LENGTH: 27
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 9

Gly Ala Leu Phe Leu Gly Phe Leu Gly Ala Ala Gly Ser Thr Met Gly
1               5                   10                  15

Ala Trp Ser Gln Pro Lys Ser Lys Arg Lys Val
            20                  25
```

-continued

```
<210> SEQ ID NO 10
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 10

Arg Arg Arg Arg Arg Arg Arg Arg Arg
1               5


<210> SEQ ID NO 11
<211> LENGTH: 6
<212> TYPE: PRT
<213> ORGANISM: Artificial Sequence
<220> FEATURE:
<223> OTHER INFORMATION: Description of Artificial Sequence: Synthetic
      6xHis tag

<400> SEQUENCE: 11

His His His His His His
1               5


<210> SEQ ID NO 12
<211> LENGTH: 27
<212> TYPE: PRT
<213> ORGANISM: Artificial Sequence
<220> FEATURE:
<223> OTHER INFORMATION: Description of Artificial Sequence: Synthetic
      peptide vector

<400> SEQUENCE: 12

Gly Ala Leu Phe Leu Gly Phe Leu Gly Ala Ala Gly Ser Thr Met Gly
1               5                   10                  15

Ala Trp Ser Gln Pro Lys Ser Lys Arg Lys Val
            20                  25
```

GENE SILENCING BY SINGLE-STRANDED POLYNUCLEOTIDES

CROSS-REFERENCE TO RELATED APPLICATIONS

This application continuation of U.S. application Ser. No. 12/525,652, filed Aug. 3, 2009, which is a 35 U.S.C. §371 national phase application of PCT/US2008/052863 (WO 2008/095192), filed on Feb. 1, 2008, each entitled "Gene Silencing by Single-Stranded Polynucleotides," which application claims the benefit of U.S. Provisional Application Ser. No. 60/898,674, filed Feb. 1, 2007, each of which are incorporated herein by reference in its entirety.

STATEMENT REGARDING FEDERALLY SPONSORED RESEARCH OR DEVELOPMENT

This invention was made in part with government support from the National Institutes of Health under Grant No. NIH GRANT R43 CA119556. The United States Government may have certain rights in the invention.

TECHNICAL FIELD

The present invention relates to the field of gene silencing and concurrent activation of RNAi and antisense pathways in a cell, via a single-stranded polynucleotide delivered to the nucleus of the cell.

BACKGROUND

Oligonucleotide compounds have important therapeutic applications in medicine. Oligonucleotides can be used to silence genes that are responsible for a particular disease. Gene silencing prevents formation of a protein by inhibiting translation. Importantly, gene-silencing agents are a promising alternative to traditional small, organic compounds that inhibit the function of the protein linked to the disease. Antisense, small interfering RNAs (siRNAs), microRNAs (miRNAs), small hairpin RNAs (shRNAs) are examples of oligonucleotides that prevent the formation of proteins by gene silencing.

The most studied antisense molecules are oligodeoxynucleotides. Antisense oligodeoxynucleotides are believed to cause a reduction in target RNA levels principally through the action of RNase H, an endonuclease that cleaves the RNA strand of DNA:RNA duplexes. This enzyme, thought to play a role in DNA replication, has been shown to be capable of cleaving the RNA component of the DNA:RNA duplexes in cell free systems as well as in *Xenopus* oocytes.

RNA interference (RNAi) is a powerful and specific method for silencing or reducing the expression of a target gene, mediated by small single- or double-stranded RNA molecules. These molecules, such as siRNAs, miRNAs and shRNAs, are important intermediaries in the RNAi pathway that lead to degradation of specific mRNAs through the RNA-induced silencing complex (RISC). During assembly of RISC, a single strand of the RNA molecules binds to the protein Argonaute 2 (Ago2), a key component of RISC. This strand then guides RISC to its complementary target mRNA, which is finally cleaved by the RNase activity located in the Ago2 protein, triggering its destruction.

It is known in the art that RNase H activity is quite variable between cell types. Thus a given disease state may not be a candidate for antisense therapy because the target tissue has insufficient RNase H activity. Similarly, Ago2 levels can vary significantly across cell lines. Therefore it is clear there is a need for methods and compositions to achieve gene silencing across tissue types, at clinically relevant dosages. Such methods and compositions would be useful for therapeutic purposes both in vivo and ex vivo, as well as for diagnostic reagents and research reagents, including reagents for the study of both cellular and in vitro events.

BRIEF DESCRIPTION OF THE DRAWINGS

FIG. 1 shows single-stranded chimeric polyoligonucleotides bind nuclear Ago2 in cells plated on relevant protein matrices". The figures describe in a) color confocal microscopy displaying nuclear colocalization as merged yellow to orange signal from Ago2 (red signal) with nucleic acid-associated anti Fitc signal (green). Single-stranded chimeric oligos (denoted as "mi CK2") colocalize with Ago2 in the nucleus following primary or effective nuclear delivery while single-stranded oligos delivered to the cytosol via Dotap liposomal complexes do not colocalized with Ago2 in the nucleus. 100,000 SCC-15 cells were plated on flamed coverslips precoated with 0.5 μg/sq. cm of model tumor matrix (2:1 Tenascin: Fibronectin). Cultures were fixed and processed for microscopy 24 hours after treatment as described in the text. Panel b describes western blotting of lysates prepared from cells treated as for microscopy and fractionated into nuclear and cytosolic lysates. Results support nuclear enhancement, enrichment or accumulation of Ago2 from baseline at 24 hours after treatment. Nuclear accumulation of Ago2 is also increased on protein matrices for standard siRNA delivered to nucleus relative to cytosolic delivery. Blot is representative of 3 independent experiments. Panel c described immunoprecipitation of nucleic acid-protein complexes from nuclear lysates of cells grown on protein matrices or plastic to confirm colocalization studies as true nuclear binding between Ago2 and Fitc-labeled RNAi molecules. Cells for lysates were grown in wells coated with model matrix as for microscopy and NP-40 A lysates were prepared. Lysates were incubated for 3 hours at 4° C. with 200 nM of various Fitc-labeled oligos and pulled down using Millipore "Catch and Release" columns with goat anti-Fitc antibodies. See text and axes legend for details. Bands indicate that true binding occurs in nuclear lysates between Ago2 and Fitc-labeled drug in cells grown on protein but not on plastic.

SUMMARY OF THE INVENTION

Figure 2:
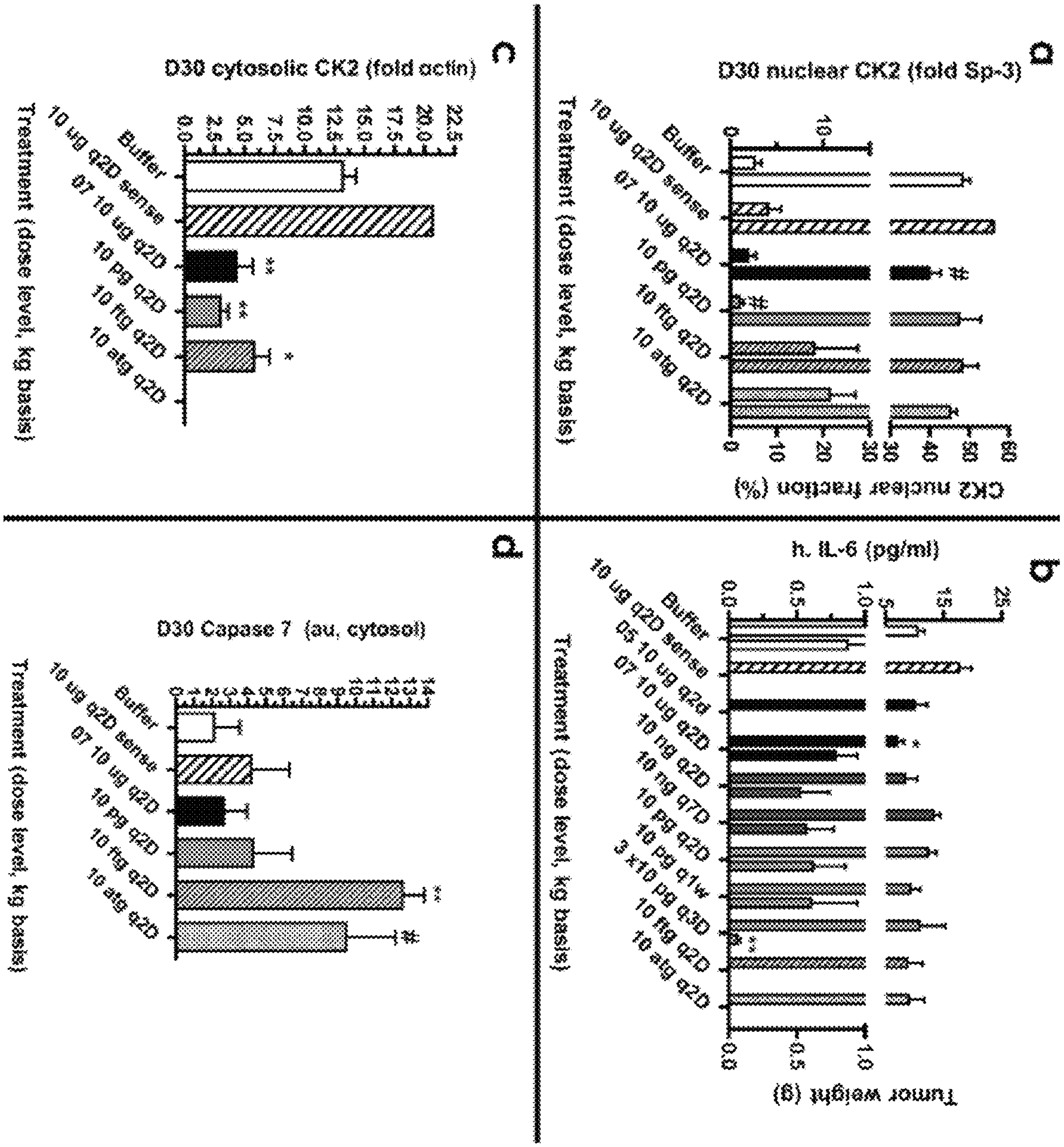
FIG. 2 shows Summary Results from FaDu Lowest Effective Dose study. Using the FaDu model of hypopharangeal cancer, a novel composition of rni CK2 was assayed for evidence of dose response. In this model, mice are flank-injected with 4 million cells and assayed with a regimen consisting of two intravenous doses started 5 days after inoculation when tumors reach 4-6 mm in diameter. A standard dosing interval of 2 days or "q2D" was used; any deviations are denoted on the figure axis. Doses are expressed on a weight basis, i.e. so that "10 pg q2D" represents two doses of 10 pg/kg of body weight over a two day interval. A similar bar pattern is used throughout bar charts for particular dosing levels. Tumor tissue and blood were collected at ~Day 30 when tumors reached 15 mm in at least one dimension and assayed for molecular changes. Tumor tissue was fractionated into cytosol and a chromatin fraction as per (Tawfic et. al, *J. Biol. Chem.* 269(10): 7489-7493, 1994). Group sizes varied from 3-6 animals and animals were tested in multiple cohorts with at least untreated controls because of the number of test conditions. Panel a) shows the effect of dose level on Day 30 levels of chromatin-bound CK2 (first bar) and chromatin-bound CK2 as a percentage of total cellular CK2 (2nd bar) from western blotting. Actin and the transcription factor SP-3 were used as loading controls. Panel b) shows the effect of dose levels on serum human IL-6 levels (a surrogate tumor marker) at Day 30 (1rst bar) and Day 30 tumor weight (2nd bar). Tumor weight was recorded in a final cohort as it was realized that surface area of resolving wounds was not representative of tumor burden. The composition used in these studies, "Formula G" was optimized for uniform particle size distribution and unexpectedly potent. Panel c) shows the effect of dose level on cytosolic levels of CK2 enzyme in Day 30 tumors. Panel d) shows the effect of dose level on cytosolic levels of Caspase 7, an apoptotic marker, in tumor tissue. Band intensities were normalized to quantities from equivalent cell lysates per membrane. Quantitation of band intensities represent two independent electrophoresis runs. Bars represent means±SE. The statistical significance of mean differences are represented as follows: "**" $p<0.01$, "*" $p<0.05$, "#" $p<0.1$

Disclosed are methods for inhibiting expression of a targeted gene, as well as methods for activating both antisense and double-stranded RNase activity. The methods include the steps of providing a bifunctional single stranded chimeric polynucleotide comprising a 3' RNA portion and a 5' DNA portion, where the bifunctional single stranded chimeric polynucleotide is capable of specifically hybridizing to the RNA sequence of the target gene, and delivering the bifunctional single stranded chimeric polynucleotide into the nucleus of the cell in an amount sufficient for degradation or inhibition of the target RNA to occur. Bifunctional single stranded chimeric polynucleotides capable of activating dsRNase as a guide strand and capable of activating RNase H are disclosed. Methods of selecting tissues and/or patients for treatment and enhancing treatment regimens with instant bifunctional single stranded chimeric polynucleotides are also disclosed.

All patents and patent applications referenced herein are incorporated by reference herein in their entireties.

DETAILED DESCRIPTION OF THE INVENTION

The present invention provides compositions for gene silencing and methods of use thereof. In particular, the invention provides bifunctional single stranded chimeric polynucleotides and methods for delivering these molecules to cells, for effective and efficient inhibition of gene expression. Additionally, the invention provides means for in vitro and in vivo applications.

The compositions and methods provided herein further expand the utility of oligonucleotide-based gene silencing technology as a tool for therapeutic applications as well as functional genomics. This discovery increases the understanding of cellular properties with respect to gene silencing function, and in view of this discovery, the present invention provides important tools to improve inhibition of gene expression in vivo and in vitro.

The present invention is based, at least in part, upon the surprising discovery that antisense and dsRNase enzyme activity can be concurrently activated by single-stranded polynucleotides comprising both RNA and DNA. The invention is further based, in part, upon the discovery that nuclear delivery of these molecules is important to effect the dual enzyme activity.

Surprisingly, we have found that RISC complexes comprised of at least Ago2 and single-stranded chimeric polynucleotides assemble in the nucleus of cells plated on relevant protein matrices (e.g., "three dimensional cell culture") following nuclear but not cytosolic delivery. Over time, a portion of the Ago2-bifunctional single stranded chimeric polynucleotide complexes shuttle to the cytosol. These findings are very surprising in light of current thinking derived from studies of cells cultured on plastic. Although structural studies of bacterial Ago proteins identify a preference or capacity in these proteins for DNA guide strands, current thinking strongly supports that i) in mammalian cells single-stranded DNA guide strands are very poorly utilized by Ago2, and ii) that cytosolic delivery of the guide polynucleotide is sufficient for Ago2 complex loading and RNAi-related gene silencing.

The instant invention is also surprising in view of the belief in the current art that extrinsic or cellular 5' phosphorylation of the guide polynucleotide is necessary for gene silencing activity and that 5' labeling will destroy RISC complex stability. Our data also highlight the usefulness of the instant in vitro methods for characterizing polynucleotide and enzyme binding. Further, the data exemplify the need for efficient bifunctional molecules given variation in level and activity of critical gene-silencing enzymes across tissues.

A bifunctional nucleic acid drug offers advantages over one with single functionality in being better able to maintain potency across tissue variations. A single-stranded polynucleic acid drug offers advantages over double-stranded polynucleic acids in terms of lower molecular weight, lower production cost, and potentially lower potential for toxicity due to the absence of potential off-targeting through the "passenger strand" or the activation of immune responses by double-stranded nucleic acids. Additionally, the low molecular weight of the nucleic acids used, and efficient nuclear delivery of them as provided by the present inventive method, allows efficacious therapy with very low dosing, resulting not only in reduced cost and toxicity, but also new treatment strategies (taking advantage of the bifunctional efficacy) such as route of administration (for example, eye drops rather than injections for treatment of diseases of the eye with nucleic acid drugs, or oral administration rather than intravenous infusion for cholesterol depletion regimens in treating cardiovascular disease).

It is reported in the art that single-stranded RNAi treatments require 10-100× higher dosages than double-stranded RNAi to achieve the same potency. Beyond medicinal chemistry and sequence efficacy, a portion of this disadvantage is attributable to the instability of the single strand moiety, an issue that may be compounded by delivery into the harsh cytosol environment. Potentially delivery of single stranded molecules to the nucleus, particularly in a capsule-type of formulation, provides a significant advantage in terms of retained potency.

So the invention may be better understood, the following terms are defined.

"Specifically hybridizable" and "complementary" are terms that are used to indicate a sufficient degree of complementarity such that stable and specific binding occurs between a single stranded chimeric polynucleotide of the present invention, and a target RNA molecule. It is understood in the art that the sequence of a polynucleotide need not be 100% complementary to that of its target RNA molecule to be specifically hybridizable. A polynucleotide is specifically hybridizable when (a) binding of the polynucleotide to the target RNA molecule interferes with the normal function of the target RNA molecule, and (b) there is sufficient complementarity so that binding of the polynucleotide to the target RNA molecule is highly selective and largely avoids non-specific binding of the polynucleotide to non-target sequences under conditions in which specific binding is desired, i.e., under conditions in which in vitro assays are performed or under physiological conditions for in vivo assays or therapeutic uses.

The term "RNA" or "RNA molecule" or "ribonucleic acid molecule" refers to a polymer of ribonucleotides. "Target RNA" refers to any RNA that can hybridize with a sufficiently complementary bifunctional single stranded chimeric polynucleotide of the present invention. Target RNA can be a pre-mRNA, pre-miRNA, pri-miRNA, mRNA, miRNA, small nuclear or cytosolic non-coding regulatory RNAs, ribosomal RNA, transfer RNAs, an hnRNA at any stage in the mRNA processing pathway, or mitochondrial RNAs. "mRNA" or "messenger RNA" is single-stranded RNA that specifies the amino acid sequence of one or more polypeptide chains. In one embodiment, the target mRNA of the invention specifies the amino acid sequence of a cellular protein (e.g., a nuclear, cytoplasmic, mitochondrial, transmembrane, or membrane-associated protein). In another embodiment, the target mRNA of the invention specifies the amino acid sequence of an extracellular protein (e.g., an extracellular matrix protein or secreted protein). The term "DNA" or "DNA molecule" or deoxyribonucleic acid molecule" refers to a polymer of deoxyribonucleotides.

The term "nucleic acid molecule" or "polynucleotide" refers to any nucleic acid containing molecule, including but not limited to, DNA or RNA. The term encompasses sequences that include any of the known base analogs of DNA and RNA The term "small interfering RNA" ("siRNA") (also referred to in the art as "short interfering RNAs") refers to an RNA (or RNA analog) comprising between about 10-50 nucleotides (or nucleotide analogs) which is capable of directing or mediating RNA interference. As used herein, the term "RNA interference" ("RNAi") refers to a selective intracellular degradation of RNA.

"Concurrent activation" and/or "bifunctional" refers to initiating, resuming or elevating two or more gene inhibition mechanisms in a given cell through the introduction of the single-stranded chimeric polynucleotide of the present invention. Those mechanisms include antisense mechanism ("antisense") and either double-stranded RNase enzymes or double-stranded RNase-related gene silencing mechanisms ("dsRNase"), or a combination thereof. The period of activation of antisense and dsRNase mechanisms within said cell may overlap in entirety, or in part, or not at all. The activation of antisense and dsRNase (or dsRNase related) mechanisms within said cell may be the result of one or more delivered bifunctional single stranded chimeric polynucleotides of the present invention affecting both mechanisms, or may be the result of a subpopulation of the delivered single stranded chimeric polynucleotides separately affecting one mechanism type, and a separate subpopulation affecting the other mechanism type, or a combination thereof. It is understood concurrent activation also contemplates potentially not activating antisense mechanism in a given cell, when enzymes or other molecules necessary for such activation, such as, for example in certain cases, RNaseH enzymes, are not present or are present in very low amounts in said cell. It is also understood concurrent activation contemplates potentially not activating dsRNase activity in a given cell, when enzymes or other molecules necessary for such activation, such as, for example in certain cases, Argonaute 2 proteins, are not present or are present in very low amounts in said cell.

"Antisense mechanism activation" refers to initiating, resuming, or elevating mechanisms of inhibiting gene expression through cleavage of complementary target RNA by RNase H enzyme activation, or by inhibition of transcription or translation, or a combination thereof. "RNase H enzyme activation" refers to initiating, resuming, or elevating silencing activity of target RNA by RNase H, an endonuclease that cleaves the RNA strand in antisense DNA:RNA hybrid duplexes. In one embodiment, RNase H is RNase H1, NCBI accession number NM_002936. In another embodiment, RNase H is RNase H2, NCBI accession numbers NM_006397, NM_024570, and NM_032192. Selective RNA degradation is induced by creating duplexes of antisense DNA:RNA that serve as substrates for cellular RNase H enzymes. The antisense strand of the DNA:RNA duplex may be comprised of DNA or, as in the present invention, be part of a DNA:RNA chimeric, and without limitations include nucleic acid modifications thereof. "Transcription inhibition" refers to mechanisms including binding of pre-mRNA leading to its degradation, or inhibition of its processing such as 5' end-capping, pre-mRNA splicing, polyadenylation, and transcriptional termination, or mechanisms leading to changes in the chromatin state of the target gene of interest, or a combination thereof. "Translation inhibition" refers to mechanisms including prevention of mRNA transport and steric hindrance of ribosomal subunit binding or other factors involved in the progression of translation complexes.

"Double-stranded RNase enzyme activation" refers to initiating, resuming, or elevating mechanisms of gene inhibition involving RNA-induced silencing complex (RISC) and related mechanisms. Methods for RISC-based gene inhibition include, but are not limited to, degradation of mRNA targets by binding of the RISC complex to the target RNA and subsequent cleavage. Mechanisms related to double-stranded RNase enzyme activation include, but are not limited to, initiating, resuming, or elevating the silencing activity of RISC by binding of RISC to target RNA and subsequent translational repression and other types of post-transcriptional gene regulation, or subsequent chromatin modification. The RISC includes at least an Argonaute family member and antisense guide strand. The present invention includes guide strand composition. "Double-stranded RNase" (dsRNase) refers to the RNA cleavage resulting from the RISC-mediated binding of the antisense RNA to target RNA.

Without wishing to be bound by theory, the term "Argonaute" refers to the mammalian Argonaute protein family currently known in the art to consist of eight members, four of which are ubiquitously expressed (Ago subfamily), with the remaining four (Piwi subfamily) being expressed in germ cells. While Ago2 has been shown to be at the core of the RISC complex that carries out oligonucleotide-guided target RNA cleavage in the region of complementarity, Ago1, 3, and 4 are thought to lack this cleavage activity and may therefore function in related oligonucleotide-guided gene silencing pathways that do not involve target RNA cleavage in the region of complementarity. Similarly, Ago2 may function in gene silencing independent of such cleavage activity, such as in translational repression. The proteins referred to herein may also be identified by their NCBI accession numbers; Ago1, NP_036331; Ago2, NP_036286, Ago3, NP_079128, and Ago4, NP_060099.

The term "nucleoside" refers to a molecule having a purine or pyrimidine base covalently linked to a ribose or deoxyribose sugar. Exemplary nucleosides include adenosine, guanosine, cytidine, uridine and thymidine. The term "nucleotide" refers to a nucleoside having one or more phosphate groups joined in ester linkages to the sugar moiety. Exemplary nucleotides include nucleoside monophosphates, diphosphates and triphosphates. The terms "polynucleotide" and "nucleic acid molecule" are used interchangeably herein and refer to a polymer of nucleotides, and in one embodiment of the present invention, are joined together by a phosphodiester linkage between 5' and 3' carbon atoms of the sugar moiety.

The term "nucleotide analog" or "altered nucleotide" or "modified nucleotide" refers to a less commonly occurring nucleotide, including natural and non-naturally occurring ribonucleotides or deoxyribonucleotides. Nucleotide analogs may be modified at any position so as to alter certain chemical properties of the nucleotide yet retain the ability of the nucleotide analog to perform its intended function. Nucleotide analogs may also comprise modifications to the sugar portion of the nucleotides. The phosphate group of the nucleotide may also be modified, e.g., by substituting one or more of the oxygens of the phosphate group with sulfur (e.g., phosphorothioates), or by making other substitutions which allow the nucleotide to perform its intended function. For use in preparing the nucleoside structural subunits of the compounds of the invention, suitable nucleobases for incorporation in these nucleoside subunits include purines and pyrimidines such as adenine, guanine, cytosine, uridine, and thymine, as well as other synthetic and natural nucleobases such as xanthine, hypoxanthine, 2-aminoadenine, 6-methyl and other alkyl derivatives of adenine and guanine, 2-propyl and other alkyl derivatives of adenine and guanine, 5-halouracil and cytosine, 5-propynyl uracil and cytosine, 6-azo uracil, cytosine and thymine, 5-uracil (pseudouracil), 4-thiouracil, 8-halo, amino, thiol, thioalkyl, hydroxyl and other 8-substituted adenines and guanines, 5-trifluoromethyl and other 5-substituted uracils and cytosines, 7-methylguanine. Further purines and pyrimidines include those disclosed in U.S. Pat. No. 3,687,808, those disclosed in the Concise Encyclopedia Of Polymer Science And Engineering, pages 858-859, Kroschwitz, J. I., ed. John Wiley & Sons, 1990, and those disclosed by Englisch et: al., Angewandte Chemie, International Edition, 1991, 30, 613.

"Phosphodiester" refers to a polynucleotide with an oxygen atom linking consecutive nucleotides. "Phosphorothiate" refers to a polynucleotide in which the oxygen atom normally linking two consecutive nucleotides has been replaced with sulfur and which resists degradation by cellular enzymes. Polynucleotidees of the present invention have their nucleoside subunits connected by phosphorus linkages from a list including phosphodiester, phosphorothioate, 3'- (or -5') deoxy-3'- (or -5')thio-phosphorothioate, phosphorodithioate, phosphoroselenates, 3'- (or -5')deoxy phosphinates, borano phosphates, 3'- (or -5')deoxy-3'- (or 5'-) amino phosphoramidates, hydrogen phosphonates, borano phosphate esters, phosphoramidates, alkyl or aryl phosphonates and phosphotriester phosphorus linkages.

The term "phosphorylated" means that at least one phosphate group is attached to a chemical (e.g., organic) compound. Phosphate groups can be attached, for example, to proteins or to sugar moieties via the following reaction: free hydroxyl group+phosphate→donor phosphate ester linkage. Also intended to be included within the scope of the instant invention are phosphate group analogs which function in the same or similar manner as the mono-, di-, or triphosphate groups found in nature.

The term "polynucleotide" refers to RNA or DNA sequences of more than 1 nucleotide in either single chain, duplex or multiple chain form. The term "polynucleotide" is also meant to encompass polydeoxyribonucleotides containing 2'-deoxy-D-ribose or modified forms thereof, RNA and any other type of polynucleotide which is an N-glycoside or C-glycoside of a purine or pyrimidine base, or modified purine or pyrimidine base or basic nucleotide. The polynucleotide may encode promoter regions, operator regions, structural regions, termination regions, combinations thereof or any other genetically relevant material that regulates or modifies chromatin or other polynucleotides. Similarly, the term "genetic" as used herein, refers to any material capable of modifying gene expression.

"Chimeric" refers but is not limited to a molecule that is composed of both RNA and DNA moieties that are naturally occurring or nucleotide analogs, linked by phosphodiester, phosphorothioate, and/or any other naturally occurring or synthetic linkage that permits the nucleotides or analogs to retain their intended function. The oligomeric or polynucleotide can be referred to as having at least a first segment and a second segment. The first segment is defined as the portion beginning at the 3' end of the polynucleotide and is the ribonucleic acid segment ad should include at least about three consecutive ribonucleotides, and the second segment is defined as the portion ending at the 5' end of the polynucleotide and is the deoxyribonucleic portion, and comprises at least about 10 consecutive deoxyribonucleotides. In one embodiment of the polynucleotide chimeric is not more than 50% ribonucleic acid. Preferred bifunctional single stranded chimeric polynucleotides in accordance with this invention preferably comprise from about 8 to about 50 nucleoside subunits. In the context of this invention it is understood that this encompasses non-naturally occurring oligomers as hereinbefore described, having 8 to 50 nucleoside subunits. It is more preferred that the bifunctional single stranded chimeric polynucleotides of the present invention comprise from about 15 to about 25 nucleoside subunits. Accordingly, bifunctional single stranded chimeric polynucleotides can be 8 nucleotides in length, 9 nucleotides in length, 10 nucleotides in length, 11 nucleotides in length, 12 nucleotides in length, 13 nucleotides in length, 14 nucleotides in length, 15 nucleotides in length, 16 nucleotides in length, 17 nucleotides in length, 18 nucleotides in length, 19 nucleotides in length, 20 nucleotides in length, 21 nucleotides in length, 22 nucleotides in length, 23 nucleotides in length, 24 nucleotides in length, 25 nucleotides in length, 26 nucleotides in length, 27 nucleotides in length, 28 nucleotides in length, 29 nucleotides in length, 30 nucleotides in length, 31 nucleotides in length, 32 nucleotides in length, 33 nucleotides in length, 34 nucleotides in length, 35 nucleotides in length, 36 nucleotides in length, 37 nucleotides in length, 38 nucleotides in length, 39 nucleotides in length, 40 nucleotides in length, 41 nucleotides in length, 42 nucleotides in length, 43 nucleotides in length, 44 nucleotides in length, 45 nucleotides in length, 46 nucleotides in length, 47 nucleotides in length, 48 nucleotides in length, 49 nucleotides in length, or 50 nucleotides in length. As will be appreciated, a "nucleoside subunit" is a nucleobase and sugar or sugar surrogate combination suitably bound to adjacent subunits through phosphorus linkages in oligoribonucleotides and through non-phosphorus linkages in oligoribonucleosides. In this context, the term "nucleoside subunit" is used interchangeably with the term "nucleoside unit" or "nucleoside." More preferably, the chimeric oligonucleotides of the invention will have nucleosides linked by naturally occurring phosphodiester linkages.

As used herein, the term "guide strand" refers to the single-stranded polynucleotide chimeric that is incorporated into RISC complex and/or related mechanisms for degradation or inhibition of target RNA.

In one embodiment, the present invention includes a non-viral carrier for delivery to the nucleus. The term "non-viral carrier" refers to any molecule or mechanical process that is able to transfer polynucleotides across the plasma membrane into the cytosol and/or nucleus of a cell that is not dependent on a virus, naturally occurring or engineered.

The bifunctional single stranded chimeric polynucleotides of the present invention may be conveniently and routinely made through the well-known technique of solid phase synthesis, see, for example, "Oligonucleotide synthesis, a practical approach," Ed. M. J. Gait, IRL Press, 1984.

In one embodiment, the method of the invention is practiced with a polynucleotide that inhibits a gene other than a Casein Kinase 2 (CK2) gene, including CK2 alpha (csnk2a1), CK2 alpha prime (csnk2a2), and/or CK2 beta (csnk2b), to treat prostate cancer and head neck cancer.

In another embodiment, the method of the invention is practiced with a polynucleotide that inhibits a gene other than a Casein Kinase 2 (CK2) gene, including CK2 alpha, CK2 alpha prime, and/or CK2 beta, to treat solid tumors. In another embodiment, the method of the invention is practiced with a polynucleotide that inhibits a gene other than a Casein Kinase 2 (CK2) gene, including CK2 alpha, CK2 alpha prime, and/or CK2 beta The following provides guidance for designing the bifunctional single stranded chimeric polynucleotides of the present invention. While not wishing to be bound by theory, it is believed that a requirement exists for a DNA end in the single-stranded bifunctional chimeric polynucleotide with a segment of RNA. This suggest a potential model where the 5' DNA end contacts the PIWI domain of Ago2 as has been described for DNA guide strand-preferring Ago2 bacterial proteins. The RNA segment, located, in one embodiment, on the 3' end, provides a higher affinity contact, potentially necessary for the additional mechanical stress that chimeric polynucleotides which are greater than 50% DNA could encounter when acting as a guide strand for dsRNase in contacting the target RNA.

Conventional antisense design typically optimizes for uniform hybridization energies across sequences at sites of low target mRNA secondary structure while siRNA design is more focused on optimizing a hybridization profile across the sequence within the context of sequence "rules". Design algorithms such as Soligo for antisense and SiRNA for siRNA are publicly available (see http:/sfold.wadsworth.org and supplier websites). Surprisingly, the inventor's data indicates sequences validated as active guide strands by derivation from functional double-stranded siRNAs as currently designed are more suitable for incorporation into this methodology than are sequences designed using tools for conventional antisense sequences acting through RNAseH or steric effects. However, an antisense sequence demonstrated successful by in vivo studies, may benefit from translation into a hybrid guide strand strategy and the capacity for binding Ago2 may be readily confirmed in vitro as described in Example 2. The sequence "LZas4" described herein provides an example of an optimized antisense validated as a species of bifunctional single stranded chimeric polynucleotide with in vivo data.

Sequence selection then consists of routine optimization in currently available double-stranded siRNA formats, followed by chemistry transfer and in vivo or in vitro assessment in target cells plated on relevant protein or 3-D matrices in combination with nuclear delivery. Peptide delivery vehicles incorporating a nuclear localization signal have been shown to function effectively to promote minimal RISC binding of single-stranded polyoligonucleotides.

A discussion of conventional siRNA sequence selection is incorporated below:

The target RNA cleavage reaction guided by siRNAs is highly sequence specific. In general, siRNA containing a nucleotide sequences identical to a portion of the target gene are preferred for inhibition. However, 100% sequence identity between the siRNA and the target gene is not required to practice the present invention. Thus the invention has the advantage of being able to tolerate sequence variations that might be expected due to genetic mutation, strain polymorphism, or evolutionary divergence. For example, siRNA sequences with insertions, deletions, and single point mutations relative to the target sequence have also been found to be effective for inhibition. Alternatively, siRNA sequences with nucleotide analog substitutions or insertions can be effective for inhibition.

Moreover, not all positions of a siRNA contribute equally to target recognition. Mismatches in the center of the siRNA are most critical and essentially abolish target RNA cleavage. In contrast, the 3' nucleotides of the siRNA do not contribute significantly to specificity of the target recognition. In particular, residues 3' of the siRNA sequence which is complementary to the target RNA (e.g., the guide sequence) are not critical for target RNA cleavage.

Sequence identity may be determined by sequence comparison and alignment algorithms known in the art. To determine the percent identity of two nucleic acid sequences (or of two amino acid sequences), the sequences are aligned for optimal comparison purposes (e.g., gaps can be introduced in the first sequence or second sequence for optimal alignment). The nucleotides (or amino acid residues) at corresponding nucleotide (or amino acid) positions are then compared. When a position in the first sequence is occupied by the same residue as the corresponding position in the second sequence, then the molecules are identical at that position. The percent identity between the two sequences is a function of the number of identical positions shared by the sequences (i.e., % homology=of identical positions/total # of positions×100), optionally penalizing the score for the number of gaps introduced and/or length of gaps introduced.

The comparison of sequences and determination of percent identity between two sequences can be accomplished using a mathematical algorithm. In one embodiment, the alignment generated over a certain portion of the sequence aligned having sufficient identity but not over portions having low degree of identity (i.e., a local alignment). A preferred, non-limiting example of a local alignment algorithm utilized for the comparison of sequences is the algorithm of Karlin and Altschul (1990) Proc. Natl. Acad. Sci. USA 87:2264-68, modified as in Karlin and Altschul (1993) Proc. Natl. Acad. Sci. USA 90:5873-77. Such an algorithm is incorporated into the BLAST programs (version 2.0) of Altschul, et al. (1990) J. Mol. Biol. 215:403-10.

In another embodiment, the alignment is optimized by introducing appropriate gaps and percent identity is determined over the length of the aligned sequences (i.e., a gapped alignment). To obtain gapped alignments for comparison purposes, Gapped BLAST can be utilized as described in Altschul et al., (1997) Nucleic Acids Res. 25(17):3389-3402. In another embodiment, the alignment is optimized by introducing appropriate gaps and percent identity is determined over the entire length of the sequences aligned (i.e., a global alignment). A preferred, non-limiting example of a mathematical algorithm utilized for the global comparison of sequences is the algorithm of Myers and Miller, CABIOS (1989). Such an algorithm is incorporated into the ALIGN program (version 2.0) which is part of the GCG sequence alignment software package. When utilizing the ALIGN program for comparing amino acid sequences, a PAM120 weight residue table, a gap length penalty of 12, and a gap penalty of 4 can be used.

Greater than 90% sequence identity, e.g., 91%, 92%, 93%, 94%, 95%, 96%, 97%, 98%, 99% or even 100% sequence identity, between the ss-siRNA and the portion of the target gene is preferred. Alternatively, the siRNA may be defined functionally as a nucleotide sequence (or oligonucleotide sequence) that is capable of hybridizing with a portion of the target gene transcript (e.g., 400 mM NaCl, 40 mM PIPES pH 6.4, 1 mM EDTA, 50 degree C. or 70 degree C. hybridization for 12-16 hours; followed by washing). Additional preferred hybridization conditions include hybridization at 70 degree C. in 1×SSC or 50 degree C. in 1×SSC, 50% formamide followed by washing at 70 degree C. in 0.3×SSC or hybridization at 70 degree C. in 4×SSC or 50 degree C. in 4×SSC, 50% formamide followed by washing at 67 degree C. in 1×SSC. The hybridization temperature for hybrids anticipated to be less than 50 base pairs in length should be 5-10 degree C. less than the melting temperature (Tm) of the hybrid, where Tm is determined according to the following equations. For hybrids less than 18 base pairs in length, Tm(degree C.)=2(# of A+T bases)+4(# of G+C bases). For hybrids between 18 and 49 base pairs in length, Tm((degree C.)=81.5+16.6(log 10[Na+])+0.41(% G+C)−(600/N), where N is the number of bases in the hybrid, and [Na+] is the concentration of sodium ions in the hybridization buffer ([Na+] for 1×SSC=0.165 M). Additional examples of stringency conditions for polynucleotide hybridization are provided in Sambrook, J., E. F. Fritsch, and T. Maniatis, 1989, Molecular Cloning: A Laboratory Manual, Cold Spring Harbor Laboratory Press, Cold Spring Harbor, N.Y., chapters 9 and 11, and Current Protocols in Molecular Biology, 1995, F. M. Ausubel et al., eds., John Wiley & Sons, Inc., sections 2.10 and 6.3-6.4, incorporated herein by reference. The length of the identical nucleotide sequences may be at least about 10, 12, 15, 17, 20, 22, 25, 27, 30, 32, 35, 37, 40, 42, 45, 47 or 50 bases.

Phosphorothioate modification of nucleoside linkages for increased stability has been reported to minimally effect silencing activity (chiu+rana, Prydz). Full substitution of PS modifications into an active single-stranded, bifunctional oligo abrogates Ago2 binding (rniLCK vs. PSLCK). While Ago2 loading of the rni (see Example 2) version of the sequence "LZas4" was poor, it was improved over the classic 2-O-Me/PS/2-O-Me gapmer design with a PS center region. A PS/2-O-Me organization may be of value in situations where PO/2-O-Me seems limited.

This analysis identifies a useful method where oligonucleotide candidate, preferably a guide strand, garnered from standard optimization techniques can be further improved in potency by an additional optimization strategy consisting of i) confirming candidate loading of Ago2 and RNAseH binding by microscopy in vitro, preliminarily with a DNA/RNA chimeric containing six 3' RNA nucleotides, ii) an optional subsequent determination of a potentially more optimal number of 3' RNA nucleotides and iii) utilization of nuclear delivery to promote Ago2 loading of the now bifunctional single-stranded oligonucleotide.

The term "oligonucleotide" refers to a short length of single-stranded polynucleotide chain. Oligonucleotides are typically less than 200 residues long (e.g., between 8 and 100.

"Polynucleotide having a nucleotide sequence encoding a gene," means a nucleic acid sequence comprising the coding region of a gene, i.e., the nucleic acid sequence that encodes a gene product.

The term "completely complementary," for example when used in reference to a bifunctional single stranded chimeric polynucleotide of the present invention refers to a single stranded polynucleotide chimeric where all of the nucleotides are complementary to a target sequence (e.g., a gene). It is understood that a single stranded polynucleotide chimeric as described in the present invention need not be 100% complementary to its target RNA sequence to be specifically hybridizable.

The term "partially complementary," for example when used in reference to a single stranded polynucleotide chimeric of the present invention, refers to a single stranded polynucleotide chimeric where at least one nucleotide is not complementary to the target sequence. The bifunctional single stranded chimeric polynucleotides of the invention, in one embodiment, will comprise at least a portion that is completely complementary to a target RNA. The remainder of the polynucleotide may be partially complementary or non-complementary or a combination. Described elsewhere are methods for designing oligos that are sufficiently complementary to be useful in the present invention and such design skills are within the purview of one of skill in the art.

The term "gene" refers to a nucleic acid (e.g., DNA) sequence that comprises coding sequences necessary for the production of a polypeptide, precursor, or RNA (e.g., rRNA, tRNA, and other ncRNAs). The polypeptide can be encoded by a full length coding sequence or by any portion of the coding sequence so long as the desired activity or functional properties (e.g., enzymatic activity, ligand binding, signal transduction, immunogenicity, etc.) of the full-length or fragment is retained.

The term "gene expression" refers to the process of converting genetic information encoded in a gene into RNA (e.g., mRNA, rRNA, tRNA, or snRNA) through "transcription" of the gene (i.e., via the enzymatic action of an RNA polymerase), and for protein encoding genes, into protein through "translation" of mRNA. Gene expression can be regulated at many stages in the process. "Up-regulation" or "activation" refers to regulation that increases the production of gene expression products (i.e., RNA or protein), while "down-regulation" or "repression" refers to regulation that decrease production. Molecules (e.g., transcription factors) that are involved in up-regulation or down-regulation are often called "activators" and "repressors," respectively.

The term "inhibition of gene expression" refers to conditions where a bifunctional chimeric single stranded polynucleotide of the present invention hybridizes to a gene and provides partial or completed loss of function of said gene. It is understood that an oligomeric compound of the invention need not be 100% complementary to its target RNA sequence to be specifically hybridizable. A reduction of target gene expression by at least 10%, 25%, 50%, 60%, 70%, 80%, 90%, 95%, or 99% is desired relative to the level of expression in the absence of the bifunctional chimeric single stranded polynucleotides of the present invention. The present invention is not limited to the inhibition of expression of a particular gene.

As used herein, the term "delivering to the nucleus of a cell" refers to the single stranded polynucleotide chimeric of the present invention localizing in the nucleus after introduction into the cell. In instances where a plurality of single stranded polynucleotide chimerics are introduced into the cell, this term refers to about ten percent or more, about twenty percent or more, about thirty percent or more, about forty percent or more, about fifty percent or more, of the molecules localizing in the nucleus. It is understood that this term includes instances where initial delivery of the single stranded polynucleotide chimeric is to subcellular areas other than the nucleus, such as the perinuclear region, wherein substantial cargo thereafter migrates to the nucleus prior to activation of gene inhibition mechanisms. It is also understood that this term includes the cellular pathway used for trafficking by the single stranded polynucleotide to the nucleus or perinuclear region prior to activation of the gene inhibition mechanisms. It is also understood that delivery to the nucleus of the cell includes methods that delivery a plurality, but not all of, a cargo to the nucleus and that once delivered to the nucleus, the bifunctional chimeric single stranded polynucleotides of the invention may then leave the nucleus, either by passive diffusion or active transport by natural systems.

Methods by which to deliver oligonucleotides to the nucleus of the cell are known in the art and all such methods are potentially adaptable to the instant invention by those of skill in the art. In one embodiment, a method by which to deliver oligonucleotides, including oligonucleotides of the present invention, into the nucleus includes delivery by sub-50 nm nanocapsules known in the art. Such capsules are described in, for example, the following U.S. patents and patent applications and are incorporated herein by reference in their entireties: Unger, U.S. Pat. No. 6,632,671, issued Oct. 14, 2003; as well as U.S. Patent Publication Nos. 20070098713, 20060018826, 20040137071, 20040038406, 2004038303, 20040023855, and 20030170893. Examples of such nanocapsule manufacture are disclosed herein in the Examples section.

Other nuclear delivery methods include, for example, use of the cell penetrating peptide MPG for nuclear delivery as described in U.S. Pat. No. 6,841,535 and used as known in the art, e.g., as described in Simeoni et al., (*Nucleic Acids Research,* 2003, Vol. 31, 2717-2724). There are at least 20 peptides that increase the delivery of oligonucleotides to cells and many of these direct nuclear delivery. See U.S. Pat. No. 6,867,043, which is incorporated herein by reference, for more details on known peptide delivery vehicles. Fusion peptides comprising regions for nucleic acid condensation, cellular targeting and nuclear localization are readily assembled using common techniques of protein engineering for targeted, nuclear delivery of polynucleotides in nanoparticles complexes. See Kumar et. al, *Nature* 448 39-43, 2007 for effective example of in vivo application, readily transferable to other organ systems.

Delivery vehicles useful for efficient nuclear delivery of single-stranded chimeric oligos, including both peptide transduction domains and s50 protein nanocapsules traffic via caveolae aka lipid raft vesicles in cells grown on relevant protein matrices or 3-D culture. A relevant protein matrices refers to proteins that primarily comprise the extracellular matrix contacted by the target cell in vivo. This will vary by target cell type, but matrices for tumor cells are provided in this application. Plating cells on relevant protein or protein-coated scaffold induces many changes in cells, including architectural and spatial changes as well changes in the proteins expressed and relative levels of expression. Caveolae are small (<60 nm) invaginations in the cell membrane that can pinch off and traffic through the cell. Caveolar transport is distinctly different from that of clathin-coated pits in that it is a recycling pathway and not destructive. Caveolae are believed to proceed both from existing invaginations and binding events in receptors segregated into cholorsterol domains known as lipid rafts (hence the alternate name of lipid raft vesicle). Caveolae are identified at the EM level and also by the presence of characteristic proteins from the caveolin/cavatellin family of proteins, including such members as flotillin and Mal. While all cells do not strictly speaking have caveolae, all cells have caveolae-like structures or lipid raft vesicles for recycling purposes. While not wishing to be bound by theory, we have observed colocalization of Fitc-labeled ss chimeric oligonucleotides, Ago2 and caveolin in cells treated with both s50 protein nanocapsules and protein transduction domain nanoparticles suggesting that lipid raft-based delivery systems will be preferred for execution of effective single-stranded guide strand loading into Risc. These delivery systems will necessarily be somewhat size-restricted because of the small size of caveolae, but several chemistries are well-known in the art to provide execution. Because of caveolae and lipid raft are downregulated tremendously by multiple logs in cells plated on plastic, partial restoration of cellular architechture by 3-D plating practice enables more effective in vitro modeling and methods to accomplish are provided in this application. Because, even 3-dimensional plating practice cannot completely reconstitute cellular membranes, we show that in vitro results from 3D culture can provide rank order guidance to in vivo studies.

Because of the focus on nanoparticles delivery to larger vesicles, e.g. cationic liposomes via clathrin-coated pits, the importance of ultra-small particle size has not been fully recognized in the art. In the present application, we provide surprising in vivo results for a new nanoparticle composition of highly uniform, ultra-small particles. These data teach the importance of uniform particle size and effects on activity.

In one embodiment, the stabilization solution during manufacturing of the above-identified nanocapsules include $Sr^{+3}$ in the stabilization solution 7.5 nM and the $Mg^{2+}$ is 2.3 nM before incubating the capsules with nominal rotation for 48 hours before centrifugation was used. Sequences manufactured as chimeric polynucleotides were optionally not propyl 3' end-blocked.

The term "in vitro" has its art recognized meaning, e.g., involving purified reagents or extracts, e.g., cell extracts. The term "in vivo" also has its art recognized meaning, e.g., involving living cells, e.g., immortalized cells, primary cells, cell lines, and/or cells in an organism.

"Cells," "host cells" or "recombinant host cells" are terms used interchangeably herein. It is understood that such terms refer not only to the particular subject cell but to the progeny or potential progeny of such a cell. Because certain modifications may occur in succeeding generations due to either mutation or environmental influences, such progeny may not, in fact, be identical to the parent cell, but are still included within the scope of the term as used herein.

As used, the term "eukaryote" refers to organisms distinguishable from "prokaryotes." It is intended that the term encompass all organisms with cells that exhibit the usual characteristics of eukaryotes, such as the presence of a true nucleus bounded by a nuclear membrane, within which lie the chromosomes, the presence of membrane-bound organelles, and other characteristics commonly observed in eukaryotic organisms. Thus, the term includes, but is not limited to such organisms as fungi, protozoa, and animals (e.g., humans).

The phrase "therapeutically-effective amount" as used herein means that amount of a compound, material, or composition comprising a compound of the present invention which is effective for producing some desired therapeutic effect in at least a sub-population of cells in an animal at a reasonable benefit/risk ratio applicable to any medical treatment.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

The phrase "pharmaceutically-acceptable carrier" as used herein means a pharmaceutically-acceptable material, composition or vehicle, such as a liquid or solid filler, diluent, excipient, manufacturing aid (e.g., lubricant, talc magnesium, calcium or zinc stearate, or steric acid), or solvent encapsulating material, involved in carrying or transporting the subject compound from one organ, or portion of the body, to another organ, or portion of the body. Each carrier must be "acceptable" in the sense of being compatible with the other ingredients of the formulation and not induce adverse events in the treated host.

As used herein, the term "subject" refers to any animal (e.g., a mammal), including, but not limited to, humans, non-human primates, rodents, and the like, which is to be the recipient of a particular treatment. Typically, the terms "subject" and "patient" are used interchangeably herein in reference to a human subject.

As used herein, the term "non-human animals" refers to all non-human animals including, but are not limited to, vertebrates such as rodents, non-human primates, ovines, bovines, ruminants, lagomorphs, porcines, caprines, equines, canines, felines, ayes, etc. and non-vertebrate animals such as drosophila and nematode. In some embodiments, "non-human animals" further refers to prokaryotes and viruses such as bacterial pathogens, viral pathogens.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

The discovery of methods and compositions capable of concurrently activating more than one mechanism of gene inhibition in a cell, with a single nucleic acid molecule, creates significant opportunities for new uses of nucleic acid therapy. The present invention provides, for example, means for characterizing the gene silencing capacity of a given cell type with regard to, for example, Ago2 and RNase H1 activity levels, and implementing optimized nucleic acid designs and application regimens incorporating the polynucleotide of the present invention in proportion to the measured activity levels. This is an advantageous and attractive approach, for several reasons. First, the resulting regimen would reflect the cell's "disease fighting" capacity, not just the cell's "disease protein signals" or "disease load" (such as, for example, tumor size in a cancer patient). Second, there would be significant advantages in incorporating a single-stranded molecule rather than a double-stranded molecule in such a regimen, including lower molecular weight, lower production cost, and lower potential for toxicity due to the absence of potential off-targeting through the "passenger strand," or the activation of immune responses by double-stranded nucleic acids. Third, the low molecular weight of the nucleic acids used, and efficient nuclear delivery of them as provided by the present inventive method, allows efficacious therapy with very low dosing, resulting not only in reduced cost and toxicity, but also new treatment strategies (taking advantage of the bifunctional efficacy) such as route of administration (for example, eye drops rather than injections for treatment of diseases of the eye with nucleic acid drugs, or oral administration rather than intravenous infusion for cholesterol depletion regimens in treating cardiovascular disease). Fourth, a given disease state (and patient) that today may not be a candidate for nucleic acid therapy, because the target tissue has relatively low RNase H activity or relatively low dsRNase activity, would have a greater chance of becoming treatment eligible if the regimen included a bifunctional polynucleotide delivered in accordance with the methods of the invention.

Similarly, given that antisense and dsRNase or dsRNase-related activities can be rate limiting and may have adverse effects on the corresponding endogenous biological pathways that these nucleic acid tools make use of, the use of polynucleotides of the present invention potentially can be used as a synergistic strategy, silencing a given gene target by harnessing two distinct mechanisms or, alternatively, could be used to target two different genes with just one polynucleotide of the present invention. Potential synergistic effects could be realized in, for example, antiviral applications.

In one embodiment, the invention includes a method of activating antisense and double-stranded RNase activity toward a target RNA. This includes the following steps, in any order. In one step, a bifunctional single stranded chimeric polynucleotide comprising a 3' RNA portion and a 5' DNA portion, wherein the bifunctional single stranded chimeric polynucleotide is capable of specifically hybridizing to the target RNA, is provided. In another step, the bifunctional single stranded chimeric polynucleotide is delivered into the nucleus of the cell. The bifunctional single stranded chimeric polynucleotide is capable of activating dsRNase as a guide strand and also, the bifunctional single stranded chimeric polynucleotide, when duplexed with the target RNA, is capable of activating RNase H.

In another embodiment of the instant invention, provided is a method for inhibiting expression of a targeted gene. This includes the following steps, in any order. In one step, a bifunctional single stranded chimeric polynucleotide comprising a 3' RNA portion and a 5' DNA portion, wherein the bifunctional single stranded chimeric polynucleotide is capable of specifically hybridizing to the target RNA, is provided. In another step, the bifunctional single stranded chimeric polynucleotide is delivered into the nucleus of the cell. The bifunctional single stranded chimeric polynucleotide is capable of activating dsRNase as a guide strand and also, the bifunctional single stranded chimeric polynucleotide, when duplexed with the target RNA, is capable of activating RNase H.

Compounds of the invention can be utilized as diagnostics, therapeutics and as research reagents and kits. They can be utilized in pharmaceutical compositions by adding an effective amount of a compound of the invention to a suitable pharmaceutically acceptable diluent or carrier. They further can be used for treating organisms having a disease characterized by the undesired production of a protein. The organism can be contacted with a compound of the invention having a sequence that is capable of specifically hybridizing with a strand of target nucleic acid that codes for the undesirable protein.

In one embodiment, the cell is in a 3-D cell culture. Conventional 2-D tissue cultures grow in monolayers on the bottom or sides of vessels in a two-dimensional architecture resulting in a flat, two-dimensional (2-D) sheet of cultured cells, or as cells growing individually suspended in media. Three-dimensional tissue culture of complex cells in three dimensions may be achieved by methods known in the art, e.g., substrate of sponge matrices, collagen gels and what are known as organ culture systems on filters or meshes. In addition, cell suspensions can be converted into multicellular spheroids, another form of three-dimensional culture. The resulting system provides an "in vivo" environment for the full differentiation of the tissue.

In one embodiment, the cell is in vivo or ex vivo.

The formulation of therapeutic compositions of the present invention, and their subsequent administration is believed to be within the skill of those in the art. In general, for therapeutics, a patient in need of such therapy is administered a compound in accordance with the invention, commonly in a pharmaceutically acceptable carrier, in dosages and novel regimen strategies as described elsewhere herein. In one embodiment of the present invention, administration is determined per kg of body weight depending on the age of the patient and the severity of the disease state being treated.

In one embodiment, the bifunctional single stranded chimeric polynucleotide is delivered at a dose of less than about 10 μg/kg body weight. In other embodiments, the single stranded chimeric polynucleotide is delivered at a dose of less than about 1 μg/kg body weight, less than about 100 nanogram(ng)/kg body weight, less than about 10 ng/kg body weight, less than about 1 ng/kg body weight less than about 100 picogram(pg)/kg body weight, less than about 10 pg/kg body weight, less than about 1 pg/kg body weight less than about 100 femtogram(fg)/kg body weight, less than about 10 fg/kg body weight, less than about 1 fg/kg body weight less than about 100 attogram(ag)/kg body weight, less than about 10 ag/kg body weight, less than about 1 ag/kg body weight.

In another embodiment, the bifunctional single stranded chimeric polynucleotide is delivered at a dose of between about 1 μg/kg body weight and about 1 attog/kg body weight. In other embodiments, dosages are between 100 ng/kg body weight and about 10 ag/kg body weight. In other embodiments, dosages are between about 10 nanogram(ng)/kg body weight and about 100 attogram(ag)/kg body weight. In other embodiments, dosages are between about 1 ng/kg body weight and about 1 fg/kg body weight. In another embodiment, dosages are between about 100 picogram(pg)/kg body weight and about 10 femtogram(fg)/kg body weight. In other embodiments, dosages are between about 10 pg/kg body weight and about 100 fg/kg body weight. In other embodiments, dosages are between about 1 pg/kg body weight and about 10 fg/kg body weight.

In some embodiments, the bifunctional single stranded chimeric polynucleotide is formulated as a pharmaceutical composition which contains a pharmaceutically acceptable carrier. Such a pharmaceutically acceptable carrier includes, for example, the sub-50 nanocapsules as described elsewhere herein.

Further, the treatment regimen may last for a period of time which will vary depending upon the nature of the particular disease, its severity and the overall condition of the patient, and may extend from once daily to once every 20 years. Following treatment, the patient is monitored for changes in his/her condition and for alleviation of the symptoms of the disease state. The dosage of the compound may either be increased in the event the patient does not respond significantly to current dosage levels, or the dose may be decreased if an alleviation of the symptoms of the disease state is observed, or if the disease state has been ablated.

In some cases it may be more effective to treat a patient with a compound of the invention in conjunction with other traditional therapeutic modalities. For example, a patient being treated for a viral disease may be administered a compound of the invention in conjunction with a known antiviral agent, or a patient with atherosclerosis may be treated with a compound of the invention following angioplasty to prevent reocclusion of the treated arteries.

Following successful treatment, it may be desirable to have the patient undergo maintenance therapy to prevent the recurrence of the disease state, wherein the compound of the invention is administered in maintenance doses, ranging from 0.01 .mu.g to 100 g per kg of body weight, once or more daily, to once every 20 years.

The pharmaceutical compositions of the present invention may be administered in a number of ways depending upon whether local or systemic treatment is desired and upon the area to be treated. Administration may be topical (including ophthalmic, vaginal, rectal, intranasal, transdermal), oral or parenteral. Parenteral administration includes intravenous administration, subcutaneous, intraperitoneal or intramuscular injection, or intrathecal or intraventricular administration.

Formulations for topical administration may include transdermal patches, ointments, lotions, creams, gels, drops, suppositories, sprays, liquids and powders. Conventional pharmaceutical carriers, aqueous, powder or oily bases, thickeners and the like may be necessary or desirable. Coated condoms, gloves and the like may also be useful. Compositions for oral administration include powders or granules, suspensions or solutions in water or non-aqueous media, capsules, sachets or tablets. Thickeners, flavoring agents, diluents, emulsifiers, dispersing aids or binders may be desirable.

Compositions for intrathecal or intraventricular administration may include sterile aqueous solutions which may also contain buffers, diluents and other suitable additives.

Formulations for parenteral administration may include sterile aqueous solutions which may also contain buffers, diluents and other suitable additives.

Dosing is dependent on severity and responsiveness of the disease condition to be treated, with the course of treatment lasting from several days to several months, or until a cure is effected or a diminution of disease state is achieved. Optimal dosing schedules can be calculated from measurements of drug accumulation in the body of the patient. Persons of ordinary skill can easily determine optimum dosages, dosing methodologies and repetition rates. Optimum dosages may vary depending on the relative potency of individual compounds, and can generally be estimated based on EC50 found to be effective in in vitro and in vivo animal models. Dosages may be given once or more daily, weekly, monthly or yearly, or even once every 2 to 20 years.

In one embodiment, the present invention is useful for treating any condition in which inhibiting a target gene is potentially of use. In one embodiment, the present invention may be used for treating a proliferative disease. By "proliferative disease" is meant any human or animal disease or disorder, affecting any one or any combination of organs, cavities, or body parts, which is characterized by single or multiple local abnormal proliferations of cells, groups of cells, or tissues, whether benign or malignant. There are many disorders associated with a dysregulation of cellular proliferation. The conditions of interest include, but are not limited to, the following conditions. In one embodiment, proliferative disease includes proliferation and/or migration of smooth muscle cells, and/or inflammatory cells into the intimal layer of a vessel, resulting in restricted blood flow through that vessel, i.e. neointimal occlusive lesions. Occlusive vascular conditions of interest include atherosclerosis, graft coronary vascular disease after transplantation, vein graft stenosis, peri-anastomatic prosthetic graft stenosis, restenosis after angioplasty or stent placement, and the like. Other proliferative diseases include abnormal angiogenesis, notably tumor growth (including tumor nests) and metastasis, and other conditions in which blood vessel proliferation is increased, such as diabetic retinopathy, psoriasis and arthropathies. Other proliferative diseases include those where there is hyperproliferation and tissue remodelling or repair of reproductive tissue, e.g. uterine, testicular and ovarian carcinomas, endometriosis, squamous and glandular epithelial carcinomas of the cervix, etc. Proliferative diseases include cirrhosis of the liver (a condition in which scarring has overtaken normal liver regeneration processes), treatment or inhibition of keloid (hypertrophic scar) formation (disfiguring of the skin in which the scarring process interferes with normal renewal), psoriasis (a common skin condition characterized by excessive proliferation of the skin and delay in proper cell fate determination), benign tumors, fibrocystic conditions, and tissue hypertrophy (e.g., prostatic hyperplasia).

Examples of proliferative diseases, disorders, and/or conditions that can be treated, prevented, and/or diagnosed by the particles of the present invention include, but are not limited to neoplasms located in the: colon, abdomen, bone, breast, digestive system, liver, pancreas, peritoneum, endocrine glands (adrenal, parathyroid, pituitary, testicles, ovary, thymus, thyroid), eye, head and neck, nervous (central and peripheral), lymphatic system, pelvic, skin, soft tissue, spleen, thoracic, and urogenital. Similarly, other hyperproliferative diseases, disorders, and/or conditions can also be treated, prevented, and/or diagnosed by particles of the present invention. Examples of such hyperproliferative diseases, disorders, and/or conditions include, but are not limited to: hypergammaglobulinemia, lymphoproliferative diseases, disorders, and/or conditions, paraproteinemias, purpura, sarcoidosis, Sezary Syndrome, Waldenstron's Macroglobulinemia, Gaucher's Disease, histiocytosis, and any other hyperproliferative disease, besides neoplasia, located in an organ system listed above.

In one embodiment, the method of the invention is practiced to treat a disease other than solid tumor cancer.

In another embodiment, the present invention includes a method of selecting a dosage level for a tissue selected for inhibiting expression of a targeted gene with a bifunctional single stranded chimeric polynucleotide, comprising the steps of: characterizing the tissue for the amount of any of the following genes: Argonaute 2, RNase H1, or a combination; and selecting a dosage level of bifunctional single stranded chimeric polynucleotide treatment based on the amount of Argonaute 2, RNase H1, or a combination present in the tissue. In addition to Argonaute 2 or RNase H1, any other protein including RNase H2 involved in gene silencing can be characterized and used in this embodiment.

In another embodiment, the method includes wherein the dosage of bifunctional single stranded chimeric polynucleotide is adjusted to an amount sufficient for degradation of the target gene to occur by an RNAi mechanism where the tissue has an amount of Argonaute2 that indicates functional RNAi activity.

In another embodiment, the method includes wherein the dosage of bifunctional single stranded chimeric polynucleotide is adjusted to an amount sufficient for degradation of the target gene to occur by an antisense mechanism where the tissue has an amount of Argonaute2 that does not indicate functional RNAi activity or where the tissue has an amount of RNase H1 that indicates functional antisense activity.

In yet another aspect, the invention provides a method for deriving information about the function of a gene in a cell or organism. The method includes the steps of: (a) introducing into said cell or organism a single-stranded small interfering RNA molecule (ss-siRNA), wherein the sequence of said ss-siRNA molecule is sufficiently complementary to a target mRNA sequence to direct target-specific RNA interference (RNAi) and wherein the 5' nucleotide is 5' phosphorylated or is capable of being 5' phosphorylated in situ or in vivo; (b) maintaining the cell or organism under conditions such that target-specific RNAi can occur; (c) determining a characteristic or property of said cell or organism; and (d) comparing said characteristic or property to a suitable control, the comparison yielding information about the function of the gene.

Various methodologies of the instant invention include step that involves comparing a value, level, feature, characteristic, property, etc. to a "suitable control", referred to interchangeably herein as an "appropriate control". A "suitable control" or "appropriate control" is any control or standard familiar to one of ordinary skill in the art useful for comparison purposes. In one embodiment, a "suitable control" or "appropriate control" is a value, level, feature, characteristic, property, etc. determined prior to performing an RNAi methodology, as described herein. For example, a transcription rate, mRNA level, translation rate, protein level, biological activity, cellular characteristic or property, genotype, phenotype, etc. can be determined prior to introducing a ss-siRNA of the invention into a cell or organism. In another embodiment, a "suitable control" or "appropriate control" is a value, level, feature, characteristic, property, etc. determined in a cell or organism, e.g., a control or normal cell or organism, exhibiting, for example, normal traits. In yet another embodiment, a "suitable control" or "appropriate control" is a predefined value, level, feature, characteristic, property, etc.

Physical methods of introducing nucleic acids include injection of a solution containing the RNA, bombardment by particles covered by the RNA, soaking the cell or organism in a solution of the RNA, or electroporation of cell membranes in the presence of the RNA.

RNA may be directly introduced into the cell (i.e., intracellularly); or introduced extracellularly into a cavity, interstitial space, into the circulation of an organism, introduced orally, or may be introduced by bathing a cell or organism in a solution containing the RNA. Vascular or extravascular circulation, the blood or lymph system, and the cerebrospinal fluid are sites where the RNA may be introduced.

The polynucleotide may be introduced in an amount which allows delivery of at least 1, 5, 10, 50, 100 or 500 polynucleotides per cell.

In another embodiment, the dosage of bifunctional single stranded chimeric polynucleotide is decreased where the tissue has an amount of dsRNase and RNAseH that indicates above average levels of both functional double stranded RNase activity and RNAseH activity. One skilled in the art will understand that the situation where higher levels of dual key mechanistic enzyme are present may result in synergy such that dose reduction is required to proactively manage subject responses.

In another embodiment, the dosage of bifunctional single stranded chimeric polynucleotide is increased where the tissue has either an amount of dsRNase that does not indicate functional double stranded RNase activity but an amount of RNase H that does indicate functional antisense activity or the reverse situation. One skilled in the art will understand that dosage may be used to compensate for loss of standard enzymatic activity but this is an advantage of this invention.

In another embodiment, the dosage of bifunctional single stranded chimeric polynucleotide is increased even more where the tissue has decreased amounts of both dsRNase and RNAseH that does not indicate either functional double stranded RNase activity or functional antisense activity. We have shown in the examples that the hybrid guide strands of the instant invention are capable of surprising enhancement of nuclear dsRNAse levels relative to baseline so that low baseline characteristic activity is not necessarily an indicator of unsuitability for treatment by this method but suggests that a dosage adjustment may be required.

While the invention has been particularly shown and described with reference to a number of embodiments, it would be understood by those skilled in the art that changes in the form and details may be made to the various embodiments disclosed herein without departing from the spirit and scope of the invention and that the various embodiments disclosed herein are not intended to act as limitations on the scope of the claims.

EXAMPLES

The following examples are provided for illustrative purposes only and are not intended to limit the scope of the invention.

Example 1

Formulation of Single-Stranded, Bifunctional Nucleic Acid Molecules for In Vitro and In Vivo Nuclear Delivery to Target Cells This example describes how illustrative colloidal formulations of diverse cargos may be generated to practice the present inventions. Nanocapsules for uptake/binding, expression and imaging studies were prepared by the "dispersion atomization" method described in U.S. Pat. No. 6,632,671, which is incorporated herein by reference in its entirety, with modifications as described herein. These particles are used for in vitro transfection studies in full serum-containing media. The cell penetrating peptide MPG for nuclear delivery is a 27-mer peptide, composed of the N-terminal domain of the HIV gp41 fusion sequence fused to the C-termain domain derived from the nuclear localization signal derived from the SV40 large-T antigen and is more fully described in U.S. Pat. No. 6,841,535 and used here according to Simeoni et al., (*Nucleic Acids Research,* 2003, Vol. 31, 2717-2724) which is incorporated herein by reference. MPG is representative of a class of useful delivery vehicles called "protein transduction agents" or peptide delivery vehicles which take advantage of highly cationic groups of amino acids to interact with cell surface receptors. There are at least 20 peptides that increase the delivery of oligonucleotides to cells and many of these direct nuclear delivery. See U.S. Pat. No. 6,867,043, which is incorporated herein by reference, for more details on known peptide delivery vehicles. Fusion peptides comprising regions for nucleic acid condensation, cellular targeting and nuclear localization are readily assembled using common techniques of protein engineering for targeted, nuclear delivery of polynucleotides.

The cell penetrating peptide MPG for nuclear delivery is a 27-mer peptide, composed of the N-terminal domain of the HIV gp41 fusion sequence fused to the C-termain domain derived from the nuclear localization signal derived from the SV40 large-T antigen and is more fully described in U.S. Pat. No. 6,841,535 and used here according to Simeoni et. al, (*Nucleic Acids Research,* 2003, Vol. 31, 2717-2724) which is incorporated herein by reference. MPG is representative of a class of useful delivery vehicles called "protein transduction agents" or peptide delivery vehicles which take advantage of highly cationic groups of amino acids to interact with cell surface receptors. There are at least 20 peptides that increase the delivery of oligonucleotides to cells and many of these direct nuclear delivery. See U.S. Pat. No. 6,867,043, which is incorporated herein by reference, for more details on known peptide delivery vehicles. Fusion peptides comprising regions for nucleic acid condensation, cellular targeting and nuclear localization are readily assembled using common techniques of protein engineering for targeted, nuclear delivery of polynucleotides in nanoparticles complexes.

For example, Kumar has developed and demonstrated the noncovalent siRNA packaging properties of protein transduction domains by synthesizing a cell-specific targeting ligand.

RVG with a poly-arginine motif for siRNA complexing (RVG-9R) (see Kumar et al., *Nature* 448 39-43, 2007). Systemic administration of RVG-9R/siRNA complexes to GFP transgenic mice resulted in siRNA passage across the blood brain barrier and knockdown of GFP within the brains of adult mice while not affecting GFP expression in other organ systems. This simple yet specific siRNA delivery approach is readily applicable to other organ systems.

Briefly, to prepare each formula below, the following procedures were used:

Formula A, 250 μg of plasmid DNA was first complexed with 36.5 μg of 25 kDa polyethyleneimine (PEI; Sigma Chemical Co., St. Louis, Mo.), a branched cationic polymer, and dispersed into 150 μl of sterile water using a water-insoluble surfactant system (TM-diol, 10 μg in DMSO or SE-30 (Air Products)). The DNA used in these experiments was a reporter plasmid containing the luciferase gene driven by the caags promoter (pultimateLuc, Nature Technology). Following emulsification with a water-miscible solvent (DMSO), the complexes were then inverted and diluted by the addition of 750 μl of PBS.

The resultant hydrophobic micelles were coated (non-covalently) by the addition of 6.3 mcg of recombinant fibrinogen fragment of tenascin (TBG; prepared by the method of Aukhill et al. (1993, J. Biol. Chem., 268:2542-53, with modifications as described herein) then atomized into a LiCl and $CaCl_2$ salt receiving solution (135 mM $Li^+$, 9 mM $Ca^{2+}$, 27.7 nM $Sr^{2+}$, 10 nM $Mg^{2+}$ (all ultrapure)). Following cold-room incubation (4° C.) with nominal rotation in 50 ml round-bottomed tubes for 48 hours, which stabilizes the coated micelles in the salt solution, the sub-50 nm nanocapsules were recovered by centrifugation at 20,000×g for 2 hrs and resuspended in PBS+10% lactitol (at a concentration of 0.5 μg/μl) for filter sterilization through a 0.2 μm filter. Alternatively, this formulation may also be prepared in a stabilization solution where the $Sr^{+3}$ in the stabilization solution is modified to 13.75 nM and the $Mg^{2+}$ is modified to 5 nM before incubating the capsules with nominal rotation for 48 hours before centrifugation. In all formulations described except Formula F, a small amount (1% of coating weight) of Syrian Hamster IgG was "spiked" into the ligand coat to enable immunodetection of nanocapsules uptake by anti-Syrian Hamster antibodies Average capsule size was less than 50 nm as measured by tapping mode atomic force microscopy using elliptical diameters of a 1 ng/ml sample dried down on a mica sheet. Most typically the average capsule size ranged from about 8 nanometers to about 30 nanometers.

Tenfibgen (TBG) Preparation:

For all formulas, TBG was prepared by the method of Aukhil with modifications, i.e. TBG was isolated and refolded from bacterial lysate by washing the insoluble pellet once with lysis buffer (50 mM Tris-HCl, 1.0 mM EDTA, 0.1 M NaCl, 0.2 mg/ml lysozyme, 0.1% Triton X-100, 0.1 mM PMSF, pH 8.0), containing 2 M urea and resuspending in 4M GuCL, 5 mM DTT in 0.02 M Tris-HCl, pH 8.0. After additional centrifugation, the clarified TBG solution was diluted with 2 M Guanidine-HCl, 20 mM Tris-HCl, pH 8.0 to make a final OD280 of about 1 and diluted dropwise about 10-fold into 20 mM Tris-HCl, 0.2 M NaCl, 0.5 M Arginine-HCl, 10 uM CuCl2 pH 8.0 for overnight stirred incubation (4° C.). After diafiltration against 20 mM Tris-HCl, pH 8.0 with an approximate 4-5 fold reduction in concentration and 0.45 uM filtration, a final purification was performed on heparan sepharose in 20 mM Tris-HCl, pH 8.0, with elution by bringing the NaCl concentration to 0.6 M.

Formula B:

sub-50 nm nanocapsules coated with TBG were generated as described in Formula A except that 12.5 mcg of TBG was added to 500 mcg of a standard unmodified siRNA oligo designed to inhibit beta-galactosidase (siβgal-1, Dharmacon) and condensed with 175 mcg of 300 MW spermine (Sigma). When generating these nanocapsules, the Tbg-coated micelles were atomized into a modified LiCl salt receiving solution (135 mM $Li^+$, 9 mM $Ca^{2+}$, 41.25 nM $Sr^{2+}$, 13.75 nM $Mg^{2+}$ (all ultrapure)) before incubating the capsules for 48 hours before centrifugation with nominal rotation. Average capsule size was less than 50 nm as measured by tapping mode atomic force microscopy using elliptical diameters of a 1 ng/ml sample dried down on a mica sheet.

Formula C:

sub-50 nm nanocapsules coated with TBG were generated as described in Formula A except that 3.1 mcg of TBG was added to 250 mcg of various sequences condensed with either 87.5 mcg 300 MW spermine (Sigma) for double-stranded variants or 63 mcg of 10 kD polyornthine (Sigma) for single-stranded sequence variants. When generating these nanocapsules, the Tbg-coated micelles were atomized into a modified LiCl salt receiving solution (70 mM $Li^+$, 14 mM $Ca^{2+}$, 39 nM $Sr^{2+}$, 17.5 nM $Mg^{2+}$ (all ultrapure)) and capsules were incubated with nominal rotation for 14.5 hours before centrifugation. Optionally, 39 nM $Sr^{2+}$ may be substituted in for single-stranded sequence variants. Capsules were resuspended following centrifugation in PBS+10% Lactitol. Average capsule size was less than 50 nm as measured by tapping mode atomic force microscopy using elliptical diameters of a 1 ng/ml sample dried down on a mica sheet.

TABLE 1a

| SEQ ID NO. | Seq. Name | Molecular Target | Sequence (5'-3')* | Citation |
|---|---|---|---|---|
| 1 | siβgal-1 | βgal | CUA CAC AAA UCA GCG AUU UUU | Mau et al., *Bioconjugate Chem*. 2006, 17, 1209-1218 |
| 2 | siZ7 | βgal | AA GCC AAU AUU GAA ACC CAC GG (P) | Griesenbach et al., *Respiratory Research*, 7:26 2006 |
| 3 | LZas4 | βgal | AAC AGg tat tcg ctg GUC AC | Supra. |
| 4 | siLamin | lamin | UGU UCU UCU GGA AGU CCA GUU CCU CCU UC (p) | Martinez et al., *Cell* 110:563-742002, |
| 5 | RFP3 | RFP | CCA AGA AGC CCG UGC AGC U (p) | This application |

*p denotes passenger strand, sense strand or mRNA target region. Lower case denotes DNA, upper case RNA. Sequences were synthesized in formats other than listed as described in the text.

Formula D:

MPG nanoparticles were prepared using the peptide vector MPG: Gly-Ala-Leu-Phe-Leu-Gly-Phe-Leu-Gly-Ala-Ala-Gly-Ser-Thr-Met Gly-Ala-Trp-Ser-Gln-Pro-Lys-Ser-Lys-Arg-Lys-Val [SEQ ID NO:12] as described in in Simeoni et al., (Nucleic Acids Research, 2003, Vol. 31, No. 11 2717-2724). Briefly, nanoparticles were prepared at a charge ratio of 10:1 (MPG: nucleic acid) by incubating 0.375 μg of ss chimeric oliogonucleotides and 14 μl of 10 μM MPG in 250 μl of serum-free media for 30 minutes at 37° C. with gentle rotation. 35 mm cultures were incubated in nanoparticles diluted 1:2 in serum-free media for 30 minutes before the addition of 500 μl of 2× serum-containing media.

Formula E:

sub-50 nm nanocapsules coated with TBG were generated as described in Formula C except that 3.1 mcg of TBG (reprecipitated in ultra-pure 40% ammonium sulfate containing 250 ppb $As^{+3}$, 25 ppm $Se^{+4}$, 2.5 ppm $Hg^{+2}$ and 25 ppm $Mo^{+5}$ for about 16 hours) was used to coat micelles.

TABLE 1b

| SEQ ID NO. | Seq. Name | Molecular Target | Sequence (5'-3')* | Citation |
|---|---|---|---|---|
| 6 | LCK | CK2 | ata caa ccc aaa ctC CAC AT | PCT/US2005/045820 |
| 7 | AsCK2 | CK2 | gtc ccg aca tgt caG ACA GG | Pepperkok, *Exp Cell Res*. 197: 245-253, 1991 |
| 8 | siLuc, a.k.a. siGL2 | luciferase | CGU ACG CGG AAU CUU CGA (p) | Ohrt et al., *NAR* 34(5), 1369, 2006 |

*p denotes passenger strand, sense strand or mRNA target region. Lower case denotes DNA, upper case RNA. Sequences were synthesized in formats other than listed as described in the text.

Formula F:

sub-50 nm nanocapsules coated with TBG were generated as described in Formula A except that 31.25 mcg of TBG (reprecipitated in ultra-pure 40% ammonium sulfate containing 250 ppb $As^{+3}$, 25 ppm $Se^{+4}$, 2.5 ppm $Hg^{+2}$ and 25 ppm $Mo^{+5}$ for about 16 hours) was added to 500 mcg of an anti-sense oligo to CK2 (phosphodiester 3' and propylend-blocked—20'ME RNA chimeric, "LCK-6", PCT/US 2005/045820) and condensed with 125 mcg of 10 kD polyornthine (Sigma). When generating these nanocapsules, the Tbg-coated micelles were atomized into a modified LiCl salt receiving solution (135 mM $Li^+$, 9 mM $Ca^{2+}$, 10 nM $Sr^{2+}$, 2.3 nM $Mg^{2+}$ (all ultrapure)) and capsules were incubated with nominal rotation for 48 hours before centrifugation. Capsules were resuspended following centrifugation in PBS+10% Lactitol. Average capsule size was less than 50 nm as measured by tapping mode atomic force microscopy using elliptical diameters of a 1 ng/ml sample dried down on a mica sheet and a surface charge of −2.7±3 mev was measured on Zetasizer 4 dynamic light scattering device at a potential of 20 volts with a 2-second pause between measurements in 1 mM KCl at 2 μg/ml.

Formula G:

sub-50 nm nanocapsules coated with TBG were generated as described in Formula A except that a stabilization solution where the $Sr^{+3}$ in the stabilization solution is modified to 7.5 nM and the $Mg^{2+}$ is modified to 2.3 nM before incubating the capsules with nominal rotation for 48 hours before centrifugation was used. Sequences manufactured as chimeric polynucleotides were optionally not propyl 3' end-blocked.

Example 2

Nuclear Delivery Creates Significant Utility for Single-Stranded Nucleic Acid Drug Species Cultures were prepared for confocal microscopy by pre-coating flame-sterilized glass coverslips, with a model tumor matrix (2:1 Tenascin:Fibronectin, Millipore CC065: Sigma F0895) at a concentration of 0.5 ug per sq. cm. in six-well plates overnight at room temperature. Cells were plated at 100,000 per well and treated 2-3 days later. Cultures were treated with 200 nM Fitc-labeled ds siRNA or oligos formulated as s50 or MPG protein nanoparticles at 50 nM as described in Example 1, Formula C-E or lipid complexes using DOTAP (Roche) per the manufacturer's instructions. Protein nanoparticles formulation utilizing nonendosomal uptake mechanisms are used to illustrate impact of nuclear delivery relative to conventional cytosolic delivery via endosomal escape following uptake by lipid complexes into clathrin-coated pits. Following treatment with either nanoparticles or lipid complexes, cultures were washed with PBS and fixed for 30 minutes in 2% paraformaldehye after 2-36 hours of incubation. The following antibodies were used to localize Fitc-labeled nucleic acids with respect to human Ago2 and RNAseH1 in various double and triple-labeling strategies: anti-Fitc (Meridian K59098G, Genetex 263445); anti-h. Ago2 (Abnova h00027161, Proteintech 10686); anti-RNAseH1 (BD 611356, Santa Cruz 30318, 30319). Slides were examined, described and ranked on a conventional Olympus microscope, before four channel imaging on a spectral confocal Nikon Clsi.

Cellular trafficking was examined in three different carcinoma cell lines, SCC-15 (derived from human tongue), Fat-1 (derived from rat nasal mucosa) and PC3-LN4 (derived from human prostate xenograft metastases) were utilized. Standard unmodified ds siRNAs against luciferase, betagal and lamin were used as positive controls and compared to ss guide strands synthesized in a 3'-(2-O-Me) RNA chimeric format using a phosphodiester backbone. For simplicity, a standard configuration of 14 DNAs linked to six 2'-O-Me RNAs was used (henceforth referred to as "rni" or RNAi oligos) as a representative species of the instant single stranded chimeric polynucleotides. Guide strands (in the rni format) were targeted against Red Fluorescent Protein (rniRFP), betagal (rnibgal, rniZ7) and a therapeutic target, the kinase CK2 (rniCK2). Key timepoints (24 hours for SCC-15s, 8 hours for PC3-LN4s) were repeated 1-2 times.

Nanocapsule delivery: In SCC-15s, we observed for s50-delivered (s50 is an alternative term for sub-50 nm nanocapsule) cargo a uniform, initial nuclear colocalization of Ago2 with both RNAi oligos (i.e., single stranded chimeric polynucleotides) and siRNAs at 8 and 24 hours posttreatment. By 36 hours, these Ago2 complexes were relocated to the cytosol. RNAi oligos also colocalized with RNAseH1, which siRNAs did not.

Baseline levels of both Ago2 and RNAseH were generally poorly detectable in untreated SCC-15 and Fat-1 cells, making shuttling more apparent than in PC3-LN4s which had much higher baselines of both enzymes. Colocalization was similar for all three cell lines, but the kinetics of cytosolic shuttling were faster in the PC3-LN4s in that complexes had moved from the nucleus by 24 hours. FIG. 1*a* shows nuclear Ago2 colocalization with ds siRNA and chimeric polyoligonucletide following nuclear delivery but not cytosolic delivery for the chimeric oligo.

Delivery via MPG peptide: MPG nanoparticles bearing 5'-labeled rnibgal and 3'-labeled siLamin were examined at 8 and 24 hours. At 24 hours in SCC-15 cells, nuclear colocalization of RNAi oligos with both Ago2 and RNaseH1 did not appear different from that of RNAi oligos formulated into s50 protein nanoparticles. At 8 hours in PC3-LN4s, uptake was not complete, however, in those cells where uptake had occurred, nuclear colocalization was extant between either RNAi oligos and the two ribonucleases or siRNA and Ago2 alone. Triple-labeling of Fitc-drug label, Ago2 and caveolin showed colocalization for both s50 and MPG nanoparticles in cells plated on relevant protein matrices. These data suggest that s50 protein nanoparticles and peptide transduction domain delivery vehicles may use similar approaches for in vivo nuclear delivery.

Interestingly, in SCC-15s and Fat-1s, RNAi oligos delivered by DOTAP complexes (representative for cytosolic delivery through endosomal escape) did not show recruitment of Ago2 to the drug in the nucleus (and thus nuclear enrichment of Ago2), and only poor recruitment of RNAseH. Using DOTAP complexes, however, good recruitment of RNAseH (but not Ago2) to the drug in the nucleus was observed in PC3-LN4s with higher baseline levels of RNaseH. RNaseH is known to show tissue-based variation in levels and substrate sensitivity. siRNA did not colocalize with RNAseH. These data suggest i) single stranded chimeric polynucleotides according to the instant invention can efficiently bind Ago2 in cells plated on relevant matrix and ii) direct or effective nuclear delivery is required for RNAi oligos to bind Ago2 forming minimal Risc complexes (see Rivas et al., Nature SMB 12(4):340-9, 2005) consistent with a concentration dependency.

To confirm and extend microscopy observations by another method, nuclear and cytosolic fractions of SCC-15s cultured on either plastic or model tumor matrix were western blotted 24 after treatment with nanoparticles and lipid complexes or immunoprecipitated following incubation of lysates with unformulated nucleic acids. Lysate preparation was similar to that used for nuclear run-on reactions using an NP-40-based lysate buffer in a procedure from (see Weinberg et al., *RNA*. 12(2):256-62, 2006) with the addition of a dounce separation. For western blotting, lysates were heated at 95 C and clarified. Nuclear pellets were resuspended in an SDS Lysis buffer (10 mM Tris-HCl [pH 7.5], 1% SDS, 100 mM DTT). Membranes were detected for Ago2, RNAseH, using the transcription factor SP-3 and actin as loading controls. Fractions were free of contaminants as indicated by appropriate location of loading control bands. RNAseH levels in SCC-15 nuclear fractions did not appear manipulated by treatments unlike Ago2 bands. Ago 2 bands were located or enriched in the nuclear fraction at 24 hours, consistent with microscopy of cells plated on relevant matrices. FIG. 1*c* shows a representative blot from one of three independent experiments. By densitometry, Ago2 levels at 24 hours, expressed as Fold Sp-3, were 1.1 (s50 rniCK2); 1.7 (s50siLuc); 0.5 (buffer); 0.5 (Dotap CK2); 1.0 (Dotap siLuc); 0.7 (Dotap). Nucleic acids were 5'-fitc labeled. As Ago2 levels are not detected in heated (or unheated) SCC-15 cytosolic lysates, the increase in nuclear levels of Ago2 may more likely result from either de novo protein production or post-binding stabilization rather than cytosolic redistribution. This experiment suggests nuclear delivery is optimal for both ds siRNA and ss chimeric polynucleotides of the present invention.

Putative nucleic acid—protein complexes were prepared by 3 hour incubation of nuclear lysates with 200 nM nucleic acid at 4° C. then immunoprecipitated using goat anti-fitc antibodies and 6-his capture reagent and nickel columns (Millipore, Catch and Release) per the manufacturer instructions. Subsequent western blot membranes were detected for Ago2 using the Abnova antibody. Ip from goat serum was used as a negative control. Equivalent density bands were detected from both ss chimeric polynucleotides against multiple targets and siRNAs using both 5' and 3' Fitc labeling strategies from lysates prepared from cell cultured on relevant protein matrices. Only barely detectable bands were observed from ip prepared using nuclear lysates from cells cultured on plastic or mixed nuclear/cytosolic lysates. These data support that colocalization results represent true binding events between ss chimeric polynucleotides, siRNA and Ago2. They also suggest that additional factors (either protein, nucleic acid, spatial or combination), present in cells cultured on matrix, but not in cells cultured on plastic, are required for efficient single-stranded guide strand binding of Ago2. FIG. 1*b* shows a representative western blot from these experiments.

These findings are very surprising in light of current thinking derived from studies of cells cultured on plastic. Although, structural studies of bacterial Ago proteins identify a preference or capacity in these proteins for DNA guide strands (see Yuan et al., *Mol. Cell,* 19:405-29, 2005), current thinking strongly supports, in mammalian cells, i) poor utilization of single-stranded guide strands by Ago2, ii) an absolute requirement for majority A-helical or RNA-like character in guide strands to facilitate cleavage, and iii) a requirement for cytosolic, rather than nuclear delivery to facilitate Ago2 complex loading.

Example 3

Incorporation of Functional Guide Strand Sequences into Nuclear-Delivered Bifunctional ss Chimeric Polynucleotides Provides Method for Executing Potent Protein Inhibition Having observed that unmodified ss chimeric polynucleotides combined with nuclear delivery to target cells creates a bifunctional RNAseH and RNAi molecule (interacts with type III dsRNAses), we sought to identify a useful procedure for application of this potentially more potent strategy to the problem of variable gene silencing and protein inhibition. A bifunctional nucleic acid drug offers advantages over one with single functionality in being better able to maintain potency across tissue variations. We were particularly interested in identifying guidelines for sequence selection and medicinal chemistry constraints. Using the experimental microscopy paradigm described in Example 2 in combination with different timepoints and the three cell lines, with formulation as described in Example 1, Formulas C-E, a series of validated antisense and siRNA sequences against multiple molecular targets were compared for their ability to bind both Ago2 and RNAseH when prepared using different chemistries. A subset of studies was performed with MPG nanoparticles and results were similar across cell lines as discussed in Example 2. The results from these colocalization studies are summarized in the following table:

TABLE 2

| | | | | Colocalization with Cargo in Nucleus | | | | |
|---|---|---|---|---|---|---|---|---|
| | | | | s50/MPG Nuclear delivery* | | Dotap Cytosolic delivery | | |
| | Sequence | | Medicinal | | | | | |
| Target | Name | Type | Chemistry | Ago2 | RNaseH | Ago2 | RNaseH | In vivo results ** |
| CK2 | rni LCK | gs | 5'-labeled hybrid | +++/ +++ | ++ | 0 | + @ 8 hr not 24 | Anti-tumor activity at 2 × 10 atg/kg by s50 capsules |
| | PSLCK | gs | 5'-labeled PS oligo | 0/0 | + to +++ | 0 | 0 to +++ | Anti-tumor activity to 2 × 1 ug without formulation. |
| | rni asCK2 | as | 5'-labeled hybrid | 0 | + | 0 | ND | No anti-tumor activity at 2 × 10 ug/kg by s50 capsules. |
| Bgal | rni sibgal | gs | 5'-hybrid | ++/ ++ | ++/ ++ | 0 | 0 | 0.5 mg/kg for siRNA, 10 ng/kg for rni by s50 in tumors for protein inhibition. |
| | rni Z7 | gs | 5'-hybrid | ND | ND | ND | ND | 100 ng/kg by s50 in tumor model for protein inhibition. |
| | rni LZas4 | as | 5'-hybrid | +/+ | ND | ND | ND | ND |
| | LZas4 | as | PS—2OMe-Gapmer (5/10/5) | 0/0 | Drug uptake# ++/0 | ND | ND | Inhibits mrna but not protein@ 160 ug via intranasal GL67 liposomes. |
| RFP | rni RFP3 | gs | 5'-hybrid | ++ | +++ | 0 | 0 | ND |
| | | gs | Hybrid-3' | +++ | +++ | 0 | 0 | ND |
| Lamin | siLamin | ds | 3'-siRNA | ++/ +++ | 0/0 | ++ | 0 | ND |
| Luc | siLuc | ds | 5'-siRNA | + | 0 | + | 0 | ND |

Abbreviations: gs (guide strand or antisense strand from ds siRNA), as (conventional antisense), ds (double-stranded species), hybrid denotes phosphodiester 2'-O—Me chimeric with six 2'-O—Me RNAs on 3' end and 5' or 3' denotes position of Fitc labeling, ND, not determined, Scale: +++ (very intense), ++ (above bkg), + (barely above bkg), 0 (signal not above bkg). PSLCK scores shown as range due to variances observed between cell lines.

*Nuclear delivery scores are shown as s50/MPG respectively. If only one score is shown, represents s50 delivery.

** Lowest dose at which specified activity, either at a gross level or at a molecular level has been observed.

#Drug uptake represents anti-fitc signal detecting presence of Fitc-labeled oligo.

Conventional antisense design typically optimizes for uniform hybridization energies across sequences at sites of low target mRNA secondary structure while siRNA design is more focused on optimizing a hybridization profile across the sequence within the context of sequence "rules". Design algorithms such as Soligo for antisense and SiRNA for siRNA are publicly available (see httpisfold.wadsworth.org and supplier websites). Inspection of the table indicates sequences validated as active guide strands by derivation from functional double-stranded siRNAs as currently designed are more suitable for incorporation into this methodology rather than sequences designed using tools for conventional antisense sequences acting through RNAseH or steric effects (compare rniLCK vs. rniasCK2 and rnisibgal vs. rniLZas4). However, a highly functional antisense sequence as demonstrated by successful in vivo studies, may benefit from translation into a hybrid guide strand strategy and the capacity for binding Ago2 may be readily confirmed in vitro as described in Example 2. The sequence "LZas4" provides an example of an optimized antisense validated with in vivo data. The guide strand/antisense pair of siZ7 and LZas4 respectively are from a publication describing a fairly intensive in vitro and in vivo optimization for anti-bgal sequences using proprietary large company software (Griesenbach et al., *Respiratory Research,* 7:26 2006).

Phosphorothioate modification of nucleoside linkages for increased stability have been reported to minimally effect silencing activity (Chiu and Rana, *RNA* 9:1035-48, 2003), We have found that full substitution of PS modifications into an active single-stranded, bifunctional oligo abrogates Ago2 binding (rniLCK vs. PSLCK). Along these lines, replacement of the classic PS-centered 2-O-Me/PS/2-O-Me gapmer design with a hybrid guide strand "rni" strategy increased Ago2 loading. However, a PS/2-O-Me organization may be of value in situations where PO/2-O-Me seems limited.

This analysis identifies a useful method where oligonucleotide candidate, preferably a guide strand, garnered from standard optimization techniques can be further improved in potency by an additional optimization strategy consisting of i) confirming candidate loading of Ago2 and RNAseH binding by microscopy in vitro, preliminarily with a DNA/RNA chimeric containing six 3' RNA nucleotides, ii) an optional subsequent determination of a potentially more optimal number of 3' RNA nucleotides and iii) utilization of nuclear delivery to promote Ago2 loading of the now bifunctional single-stranded oligonucleotide. Confirmation of Ago2 binding may be considered optional for guide strand-derived candidates, but not antisense candidates.

Example 4

Bifunctional, ss Chimeric Polynucleotides Dual Binding of RNAseH and Ago2 Corresponds with Increased Inhibition of Target Protein In Vitro in Cells Cultured on Relevant Protein Matrices The correspondence between ss chimeric polynucleotides-enzyme binding as indicated by microscopy colocalization and in vitro inhibition of target protein (betagal) was examined in mouse CT26 betagal-positive colon carcinoma cells.

Cells were plated at 12,000 cells/well with 1% fetal calf serum into 24 wells trays containing 0.3-0.5 um thick polymeric spun scaffolds coated with 100 pg/ml of 2:1 human tenascin: fibronectin protein as a relevant matrix (tumor matrix). 3-dimensional tissue scaffolds such as Ultramax (Corning, Surmodics, Donaldson Co.) can be useful for making bulk protein, RNA or enzymatic measurements under more biologically relevant conditions such as required for careful assessment of the bifunctional, ss chimeric polynucleotides. Optimization of cell culture conditions for three-dimensional matrices involves identifying plating and matrix coating conditions that produce best results in a functional activity or enzymatic assay. For example, using in vitro growth inhibition as functional assay, we have determined that rat cells perform optimally at 0.5% fetal calf serum on matrices coated with 10 pg/ml of human proteins rather than the 100 pg/ml preferred by human and feline cell lines. Future optimization with the murine CT26 line, for example, will involve consideration of 10 pg/ml coating conditions.

Cells were treated with nanoparticles of Fitc-labeled oligos used cellular trafficking studies in Example 2 and unlabeled double-stranded siRNAs. Relative change in β-galactosidase enzymatic activity was measured in lysates from cells 24 hours after 200 nM treatment as described in Simon and L is (1987, *NAR* 15: 2971-2988) using the following lysis buffer (25 mM Tris-HCL pH 7.8, 1 mM EDTA, 8 mM magnesium chloride, 1% Triton X-100, 1 mM DTT). We observed an increase in β-galactosidase activity inhibition in oligos relative siRNAs in cells plated on relevant matrices and results are summarized in Table 3. Recall from Example 2 using nuclear-delivery, ds siRNA molecules were observed to colocalize with Ago2 but not RNAseH1 while antisense oligos in conventional chemistries were observed to colocalize with RNAseH1 but not Ago2 and ss chimeric polynucleotides molecules in the 3'-RNA phosphodiester chimeric format bound both Ago2 and RNaseH1. These data are consistent with a cell line containing higher RNAseH than Ago2 levels under these conditions as the conventional antisense induced increased β-galactosidase inhibition over the siRNAs. However, in both cases (siRNA to ss chimeric polynucleotides and antisense to ss chimeric polynucleotides), the dual functionality induced by the phosphodiester ss chimeric polynucleotides format increases sequence activity supporting that optimization of candidate sequence into ss chimeric polynucleotides of the instant invention will provide a method for enhanced activity across biological variation. These data are surprising, as it is believed in the current art, that extrinsic or cellular 5' phosphorylation is required for single-stranded guide activity and that 5' labeling will destroy RISC complex stability.

These data do not distinguish between different modes of action by a dsRNAse such as Ago2, i.e. cleavage or repression as both follow from guide strand binding and result in decreased levels of target protein. Using the model rni molecule, rni CK2, we have measured significant reduction in CK2 mRNA in vitro in cells plated on 3D-scaffolds, raising the possibility that either or both modes of action in combination are feasible for bifunctional molecules. In conclusion, these data highlight the usefulness of our in vitro methods for characterizing binding and exemplify the need for bifunctional molecules given tissue variation in critical gene-silencing enzymes.

TABLE 3

| | s50 siZ7 | s50 sibgal | s50 5F-Fitc rnibgal | s50 5F-Fitc rniLZas4 | s50 5F-Fitc LZas4 |
|---|---|---|---|---|---|
| nucleic acid species | unlabeled siRNA | unlabeled siRNA | labeled rni oligo | labeled rni oligo | labeled antisense |
| Day 1 βgal activity (% control, CPRG, mean ± SE) | 104 ± 5 | 107 ± 4.2 | 69 ± 0.7 | 51 ± 0.7 | 72 ± 0.7 |
| Table 1 Ago2 binding | n/a | n/a | ++ | + | (−) |
| Table 1 RNaseH binding | n/a | n/a | ++ | ND | ++ |

Example 5

Evaluation of Importance of 3' Terminal RNA Segment in Bifunctional, ss Chimeric Polynucleotides The impact of chimeric structure on enhanced bifunctional antisense activity was assessed by comparing different phosphodiester ss chimeric polynucleotides configurations by 48 hour growth inhibition in vitro. Standard segments of six 2'-O-Me-modified RNAs were shuffled in the 20 mer anti-CK2 sequence "LCK" (Table 1b) and prepared as s50 nanocapsules for in vitro growth inhibition assay as described in Example 1, Formula E. A double-stranded siRNA type chemistry was included as a comparison. This chemistry consisted of an unmodified RNA guide strand annealed to a heavily modified DNA chimeric passenger strand. The chemistry is described in Hofgrefe et al., 2006 (*Nucleosides, Nucleotides,*

*and Nucleic Acids,* 25:889-907). Results, summarized in Table 4, indicate the 3' RNA ss chimeric polynucleotide provides the most effective growth inhibition in the range tested while the 5' RNA ss chimeric polynucleotides and RNA gapmer are 30-50% higher. The classic DNA gapmer design, (see "outer"), viewed as a standard in the art, is significantly worse than the 3' RNA chimeric.

It should be noted that while cell plating on coated 3D scaffolds may replace important factors and reconstitute cellular architecture, e.g. lipid rafts and caveolae important necessary for modeling a biological phenomenon (e.g. Argo2 cobinding drug and caveolin), matrix also can provide significant survival advantage to carcinoma cells. For example, SCC-15 tongue carcinoma cells exhibit an IC 50 of about 0.5 uM for Docetaxel when plated on plastic in full serum. No cell death is observed when cells, plated on uncoated scaffolds in reduced serum, are treated at the highest feasible stock dilution of 10 uM. It should also be noted that the model molecular target in this study, Casein Kinase 2, has an extended half-life in tumor cells (plated on plastic) of ≥5 days (see Seeber, et al., *Apoptosis* 10: 875-885, 2005) highlighting the observation that effective treatment based on protein inhibition may require consideration of protein half-life when considering the usefulness of repeat dosing While not wishing to be bound by theory, these data suggest a requirement for a DNA end in the single-stranded bifunctional oligo with a segment of RNA. This suggest a potential model where the 5' DNA end of the highly DNA guide strand contacts the PIWI domain of Ago2 as has been described for DNA guide strand-preferring Ago2 bacterial proteins (Yuan et al., *Mol Cell* 19:405-19, 2005). The RNA segment, located preferably on the 3' end provides a higher affinity contact, potentially necessary for the additional mechanical stress a highly DNA guide strand could encounter, together with as yet unknown factors, in contacting the target RNA. Interestingly, the target CK2 sequence itself, has self-complementarity in the region from which the sequence, "LCK" was derived and the true sense is a weak antisense suggesting the possibility where the 5' chimeric of "LCK" could elicit some bifunctional activity. In this example, we used a standard run of six 2'-O-Me-modified RNA for an RNA segment. This was chosen as an intermediate screening value and was also the determined optimum for the model sequence "LCK". We have arrived at optimums for different sequences using activity assays as decision-making tool, ranging from 4-10, but not 12 or greater from the 3' end for sequences of a standard 20 mer length.

TABLE 4

Growth inhibition (cell viability) in FaDu carcinoma cell lines

| Dose (uM) | "rni CK2" 3' RNA chimeric | "Forward" 5' RNA chimeric | "Inner" DNA/RNA/DNA gapmer | "Outer" RNA/DNA/RNA gapmer | "sHCK2 + 5P" ds hybrid siRNA |
|---|---|---|---|---|---|
| 20 | 46.7 ± 5 | 68.1 ± 10 | 64.1 ± 20 | 76.5 ± 9 | 72.0 ± 16 |
| 10 | 64.1 ± 17 | 81.5 ± 10 | 88.5 ± 38 | 90.0 ± 14 | 85.1 ± 30 |
| 5 | 64.4 ± 18 | 99.7 ± 16 | 118.8 ± 63 | 85.5 ± 20 | 94.2 ± 31 |
| 2.5 | 86.2 ± 24 | 87.6 ± 15 | 117.9 ± 60 | 96.1 ± 15 | 89.4 ± 12 |
| 1.25 | 71.2 ± 22 | 96.6 ± 11 | 138.1 ± 66 | 86.4 ± 12 | 79.8 ± 21 |
| 0 | 100 | 100 | 100 | 100 | 100 |

Oligonucleotides administered to 3,000 FaDu cells plated with 0.5% FCS media on matrix-coated 3-D scaffolds in 96 wells, formulated into s50 protein nanocapsules as described in Example 1, Formula E. Proliferation rates were calculated relative to sugar capsule by thymidine incorporation in the last 16 hours of the growth period. Experiment performed 2-4 times in duplicate. Values reported as Mean±SE.

Besides the impact of chemistry organization on activity of dual function hybrid guide strands, we considered the impact of biological variation in critical enzymes on ss chimeric polynucleotide activity. While not wanting to be bound by theory, it is known in the art that enzymatic processes are rate-limited by concentration, activity levels and availability of key enzymes. We noticed considerable variation in levels of RNAseH and Ago2 across cell lines by microscopy in Example 2 and asked whether there might be correspondence between intrinsic enzyme activity and sensitivity and potentially benefit from the dual function chimeric format. Using the rni CK2 sequence as a model dual function chimeric oligo, we compared enzyme rankings with chimeric activity in growth inhibition (see Table 5). The data suggests that cells containing higher baseline levels of key enzymes will require less dual function oligo for the same amount of activity. While this is an in vitro comparison, it is known that PC3s respond to the LCK sequence in vivo at levels 4 logs below those tested in head neck cancers xenograft tumors arguing a basis for synergy for dual function oligos.

TABLE 5

Growth inhibition (cell viability) in carcinoma cell lines

| Cell Line | Fat-1 | SCC-15 | PC3-LN4 |
|---|---|---|---|
| Cell Viability following challenge with 20 uM rni CK2 | 47.5 ± 42 | 68.0 ± 15 | 42.7 ± 17 |
| Cell Viability following challenge with 10 uM rni CK2 | 74.62 ± 8 | 78.0 ± 5 | 35.8 ± 22 |
| Relative baseline Ago2 Rank | 0 | + | +++ |
| Relative baseline RNaseH Rank | + | 0 | +++ |

Oligonucleotides administered to cells on 10-100 pg/ml matrix-coated 3-D scaffolds in 96 well plates, formulated into s50 protein nanocapsules as described in Example 1, Formula E with the following conditions: Fat-1, 10,000 cells, 0.5% media; SCC-15, 12,000, 1% media and PC3s, 3000 cells, 0.01% media. Proliferation rates were calculated relative to sugar capsule by thymidine incorporation in the last 16 hours of the growth period. Experiment performed 2-4 times. Values reported as Mean±SE.

We conclude these data provide a basis for treatment approaches incorporating the dual function chimeric polyoligonucleotide and assessment of relevant baseline enzymatic activities in target tissues to define appropriate personal medicines approaches.

Example 6

Reduction of Metastatic Tumor Burden with Targeted, Low Dosing in Human Xenograft Tumors Using Model Therapeutic Bifunctional ss Chimeric Polynucleotides In these examples, we have been using a subdomain of the extracellular matrix protein tenascin, i.e. tenfibgen, as a nanoparticles ligand for directing s50 particles to tumor cells. Tenascin has been linked to the vascularization of tumor tissue; specifically, tenascin (i) has been found in and around tumor microvessels, (ii) is produced by migrating endothelial cells, and (iii) when coated on tissue culture plates, stimulates sprouting by and migration of endothelial cell. Antibodies to tenascin were one of the earliest anti-angiogenic approaches explored in cancer treatment, and this therapy continues in active human clinical development.

As described below, TBG s50 nanoparticle has been demonstrated to provide specific whole body transfection, which illustrates that the strategy of using bifunctional chimeric molecules with nuclear entry s50 nanoparticles to target both RNAi and antisense mechanisms (here, Ago2-RNaseH) at low doses to minimize any side effects and provide a greater therapeutic index can also be used for therapeutic delivery of biologics to proliferating tumor cells and associated microvasculature. Also, for tissues or cancers which express varying amounts of the enzymes associated with RNAi mechanisms and antisense (such as, Ago2-RNaseH), a bifunctional molecule can help assure a therapeutic effect.

We tested sensitivity of the 3 SCCHN models to lower dose levels of nanoparticle-delivered therapeutic ss chimeric polynucleotides, by re-treatment of a small number (n=14) of mice with larger tumors remaining at the end of a survival study. Mice were retreated with repeat doses ranging from 10 ug/kg to 100 ng/kg. Best results were achieved at lower doses in the range 100 ng/kg as evidence of tumor lysis syndrome was observed at ug/kg dosing (transient dehydration, fistulas from rapidly dying visceral metastases and organ fibrosis secondary to rapid necrotic tumor death). These mice had starting tumor dimensions of 15 mm in one dimension with liver, lung or brain metastases by whole-body imaging.

Good efficacy was seen in the lowest dose groups at 100 ng/kg dosing, suggesting that an indicator of dual RNAi and antisense pathway activation is efficacy at lower doses of therapeutic in view of the catalytic action of traditional siRNA, as well as activation of antisense. Best responders were mice that had been flank-inoculated with the SCC-15 tumor (4 million cells) and previously treated with short-term chemotherapy (cisplatin+docetaxel).

To begin the retreatment study, after 6 months of the short term chemotherapy treatment, mice were selected for retreatment on the basis of positive tumor signal by imaging (by whole-body bioluminescence imaging using the Xenogen™ technique—in this technique, mice are administered plasmid DNA encoding the luciferase reporter gene nanoencapsulated in TBG using techniques described previously (particles formulated per Example 1, Formula A). The purpose was to assess the existence of remaining tumor burden sensitive to TBG uptake. After waiting 7 days to enable gene expression, mice were injected with D-luciferin contrast (the substrate for the expressed luciferin enzyme). Bioluminescence was then collected from anesthetized mice in the Xenogen™ apparatus to suggest the location of nanocapsule uptake, which in this case, would be tumor.

During active treatment, mice were reimaged every two weeks using exactly the same protocol with plasmid readministered every 4 weeks. Plasmid administration was titered during method development so as to not negatively affect tumor growth. In both cases of surviving mice, mice showed strong liver signal and in one mouse, some lymph node and kidney signal. After two to four weeks of thrice weekly 100 ng/kg intravenous injection of nanocapsule-formulated ss chimeric polynucleotides (prepared as in Example 1, Formula F), both mice were clear of liver, kidney and lymph node signal.

Following the clearance of visceral mets, the mice were treated with repeat i.p. dosing of the nanocapsule-formulated ss chimeric polynucleotides and 20 ug/kg cisplatin (and surgery for one mouse) to remove surface lesions. Occasional topical administration of a 3 ug/ml suspension of nanocapsule-formulated ss chimeric polynucleotides continued through the survival period. The two nonsurvivors of the low dose group died of complications from either surgery or a treatment-induced lung fistula from a dying met (without apparent lung fibrosis induction. These data indicate that nanoencapsulated anti-cancer therapeutics such as rni CK2 will be efficacious for treating metastatic and disseminated cancer in aggressive, clinically relevant models at ultralow dosing, suggesting that an indicator of dual RNAi and antisense pathway activation is efficacy at lower doses of therapeutic in view of the catalytic action of traditional siRNA, as well as activation of antisense.

Example 7

Bifunctional ss Chimeric Polynucleotides Exhibit High Potency In Vivo with Surprising Persistent Effect in a Model Therapeutic Sequence We further tested the anti-CK2 sequence, "LCK" (Table 1b) for evidence of a dose response in nude mice bearing FaDu flank xenograft tumors. Mice were injected with 4 million cells and treatment commenced intravenously with LCK nanoparticles made as described in Example 1, Formula G, 5 days following tumor inoculation when tumor diameters was 4-5 mm. Relative to the composition Formula F used in Example 6, Formula G was optimized to improve particle size variation as measured by both AFM. By Dynamic light scattering, a bulk measurement technique made in water rather than the dry AFM measurement, 98.4% of Formula G particles was 25.2±4.4 nm.

For activity testing with the more uniform particle size composition, Formula G, group sizes ranged from 3-6 animals and the study was conducted in multiple cohorts due to the large numbers of test conditions. Tumors were followed with caliper measurements over a period of about 30 days until tumors reached about 15 mm in at least one dimension. Then mice were euthanized and blood and tumor tissue collected for analysis. In the last cohort of animals residual tumors were additionally weighed.

Based on the anti-tumor activity demonstrated by the nanoparticle LCK sequence in the bifunctional ss chimeric polynucleotides format at repeat doses in 100 ng/kg with mice bearing large tumor burdens, we used a starting regimen of two doses with a 2 day interval (q2D) at doses ranging from 10 ug/kg to 10 attogram/kg. At a gross level, we found evidence of anti-tumor activity into the attogram range with a decrease in percentage of responders with dose rather than the pattern of response. At the molecular level, Day 30 tumor tissue was fractionated into nuclear and cytosolic fractions and western blotted for compartmental levels of CK2 and Caspase 7 to assay for evidence of apoptosis. Terminal blood was also assayed by ELISA for human IL-6 as a surrogate marker for tumor levels. Results are summarized in FIG. 2.

CK2 (Casein Kinase 2) is a ubiquitous enzyme overdriven by tumor cells to promote survival by multiple pathways and accumulates in cell nuclei under conditions of stress and in tumors. Shuttling of CK2 from the nuclear compartment precedes apoptosis and the inability of the tumor cell to maintain CK2 precedes tumor death. Flank tumors receiving higher doses showed a pattern of continued growth accompanied by swelling and subsequent necrosis with wound healing sequelae. FIG. 2*b* shows that in a later cohort, not yet analyzed by western blotting, residual tumor quantified by weight (and not wound surface area) was resolved most rapidly with 3 lower pg/kg doses rather than the two used in the standard dose ranging regimen. Residual lesions were followed for healing capacity in one individual from 4 lower dose groups and all healed over a period of 3 months without recurrence. Two of the 4 recurred in an additional 3 month period before humane euthanasia.

Although unexpected and completely surprising, the extreme potency showed by particle-optimized Formula G may be partially understood by the concept of improved particle molarity, i.e. uniform, smaller particles will the same amount of bifunctional oligo in an increased number of particles. When combined with the surprising potency of the bifunctional oligo format, the synergistic result is extremely low dosing.

Results suggest significant persistence of molecular effects in vivo with limited dosing, i.e. molecular changes persisted in tumor tissue 3 weeks after two small doses. These are very surprising results, to say the least. FIG. 2*a* shows that higher ug/kg dosing is required for persistent reduction in the nuclear fraction of CK2 enzyme, but inhibition of CK2 in the cytoplasmic compartment is observed at all dose levels quantified (FIG. 2*c*). Reduced levels of IL-6 also occurred at the 10 ug/kg dose level (FIG. 2*b*) and corresponded with decreased nuclear CK2 and is consistent with the more rapid (and problematic tumor necrosis with associated wound care in mice) observed at ug/kg doses.

At lower dosing levels of 10 ftg/kg and 10 atg/kg, ongoing apoptosis appeared to be more prevalent as 3-6 fold increases in 35 kD Caspase 7 with cleavage products were measured (FIG. 2*d*). This was consistent with less rapid and difficult-to-manage tumor death. Flank tumors receiving higher doses showed a pattern of continued growth accompanied by swelling and subsequent necrosis with wound healing sequelae. FIG. 2*b* shows that in a later cohort, not yet analyzed by western blotting, residual tumor quantified by weight (and not wound surface area) was resolved most rapidly with 3 lower pg/kg doses rather than the two used in the standard dose ranging regimen. Residual lesions were followed for healing capacity in one individual from 4 lower dose groups and all healed over a period of 3 months without recurrence. Two of the 4 recurred in an additional 3 month period before humane euthanasia.

These observations on decreased magnitude of dosing levels, while not fully explainable by current thinking on feasibility for in vivo single-stranded RNAi, or decreased potency and persistence of effect believed to be associated with standard single-stranded RNAi (see Holen et al., NAR 31(9): 2401-7, 2003), are consistent with in vitro work detailing an enhanced protein half-life for CK2 alpha in tumor cells relative to normal cells (≥5 days vs. 14 hours) and the capacity for siRNA but not conventional antisense to inhibit the tetrameric kinase's activity at doses not showing detectable changes in mRNA or protein levels (see Seeber, et al., *Apoptosis* 10: 875-885, 2005).

The increased potency of the dual chimeric polynucleotide strategy is also not consistent with any indirect immunomodulation as single 10 mg/kg doses of s50 tenfibgen particles bearing LCK sequence in the "rni" format did not any evidence of early inflammatory responses in outbred mice. While the LCK sequence contains no CpG motifs or other known immunomodulatory sequence motifs, these results still support that increased chimeric polynucleotide potency derived from dual mechanism activation rather than immunomodulation.

The surprising extreme potency showed by particle-optimized Formula G may be, in retrospect, partially understood by the concept of improved particle molarity, i.e. uniform, smaller particles will distribute the same amount of bifunctional oligo in an increased number of particles. When combined with the surprising potency of the bifunctional oligo format, the synergistic result is extremely low dosing.

Example 8

Targeted s50 Nanoparticle Lowers ss Chimeric Polynucleotide Delivery Requirements for Efficacy To investigate the usefulness of our method for enhancing potency of oligonucleotide molecules for efficacy, i.e. inhibit production of a target protein in vivo, we performed limited dose ranging studies of guide strands from published siRNA molecules formatted into the chimeric chemistry of a dual functional oligonucleotide, i.e., ss chimeric polynucleotides. We evaluated two anti-β-galactosidase sequences, "sibgal-1" and "siZ7" as rnibgal and "rniZ7" respectively (see Table 1a).

Earlier we had established an in vivo baseline for anti-betagalactosidase siRNA activity using a model system consisting of Balb/c mice inoculated with β-galactosidase-(+) CT26 tumors. The CT26 mouse colon carcinoma line, available from ATCC, has been retrovirally modified to produce β-galactosidase. The published "sibgal-1" sequence was formulated with tenfibgen nanoparticle targeting as described in Example 1 Formula E for target cell nuclear delivery according to our method. The baseline study consisted of 18 mice in 6 treatment groups. Tumors were collected 3 days after i.v. treatment of s50 nanoparticle-target siβgal oligos and processed for microscopy western blotting and qPCR. Western blotting indicated a significant 70% reduction in β-galactosidase in tumor lysates from sham-treated at a single dose of 0.5 mg/kg. QPCR indicated a reduction of more than 98% in mRNA groups. A dose of 50 ug/kg was not effective in inhibition of target protein.

Given that dual functional ss chimeric polynucleotides had exhibited increased target protein inhibition in in vitro testing, we assayed for persistence of rank order between in vitro and in vivo studies by treating a number of mice bearing CT-26 β-galactosidase-(+) tumors decreasing doses of dual functional ss chimeric polynucleotides based on the same sequence and formulated into nanoparticles for nuclear delivery as described in Example 1, Formula I-K. Tumors were allowed to grow to 4-6 nm in diameter before starting treatments. Assay results were scored by confocal fluorescence microscopy of frozen tumor sections stained with a rabbit anti-betagalactosidase antibody (Cortex, San Francisco, Calif.). Results are summarized in Table 6 below:

TABLE 6

| Test Regimen | Test Sequence | Tissue Collection (time after 1rst dose) | Result (microscopy score for βgal) | Rank Order |
|---|---|---|---|---|
| 2 × 10 ng/kg sugar nanoparticles | none | 2 or 3 days | +++ | 6 |
| 1 × 1 ug/kg | rnibgal | 3 days | 0 | 1 |
| 2 × 100 ng/kg q 24 h | rnibgal | 2 days | 0 | 2 |
| 2 × 10 ng/kg q 24 h | rnibgal | 2 days | + | 4 |
| 2 × 100 ng/kg q 24 h | rniZ7 | 2 days | 0 | 3 |
| 2 × 10 ng/kg q 24 h | rniZ7 | 2 days | ++ | 5 |

Scale:
0 = no expression;
+ = poor, dim, or patchy expression,
++ = moderate or >40% incidence,
+++ = good or >70% incidence of expression.

The data shows that additional optimization as a dual functional ss chimeric polynucleotide according to the present invention could provide significant, here ~3.5 logs, in vivo efficacy enhancement for siRNA molecules.

What is claimed is:

1. A method for inhibiting expression of a target gene in a tumor cell, wherein the target gene is Casein Kinase 2, comprising: administering a formulation of single stranded polynucleotides to a mammal in an amount sufficient to inhibit expression of the target gene in the tumor cell, wherein said formulation is prepared according to a process comprising:

employing a suitable siRNA design algorithm to identify a candidate functional double stranded siRNA to a target RNA;

synthesizing a single stranded polynucleotide sequence comprising at least a portion of the guidestrand of the candidate functional double stranded siRNA, wherein a functional single stranded polynucleotide consisting of 15-25 linked nucleosides without a self-complementary sequence region is formed; wherein the functional single stranded polynucleotide sequence comprises a 3' RNA portion and a 5' DNA portion, wherein the functional single stranded polynucleotide comprises at least three consecutive ribonucleotides at the 3' end, wherein the functional single stranded polynucleotide is at least 50% DNA, wherein each of the internucleoside linkages of the functional single stranded polynucleotide is a phosphodiester linkage; and formulating a plurality of the functional single stranded polynucleotides, in the absence of a passenger strand, with a pharmaceutically acceptable non-viral carrier;

wherein the formulation is introduced into the tumor cell, wherein the functional single stranded polynucleotides of the formulation are delivered to the perinuclear region or the nucleus of the tumor cell, whereupon said functional single-stranded polynucleotides concurrently activate dsRNAse and RNAseH mechanisms of the cell, thereby inhibiting expression of the target gene in the tumor cell.

2. The method of claim 1, wherein the functional single stranded polynucleotides do not comprise extrinsic 5' phosphorylation.

* * * * *